(12) United States Patent
Adams

(10) Patent No.: US 10,201,281 B2
(45) Date of Patent: Feb. 12, 2019

(54) SYSTEM, METHOD AND ARTICLE FOR NORMALIZATION AND ENHANCEMENT OF TISSUE IMAGES

(71) Applicant: CERNOVAL, INC., Sammamish, WA (US)

(72) Inventor: Bruce Adams, West Vancouver (CA)

(73) Assignee: Cernoval, Inc., Sammamish, WA (US)

( * ) Notice: Subject to any disclaimer, the term of this patent is extended or adjusted under 35 U.S.C. 154(b) by 0 days.

(21) Appl. No.: 15/155,725

(22) Filed: May 16, 2016

(65) Prior Publication Data

US 2016/0345833 A1 Dec. 1, 2016

Related U.S. Application Data

(63) Continuation of application No. 13/583,595, filed as application No. PCT/US2011/027512 on Mar. 8, 2011, now Pat. No. 9,339,194.

(Continued)

(51) Int. Cl.
*A61B 5/00* (2006.01)
*A61B 5/11* (2006.01)
(Continued)

(52) U.S. Cl.
CPC .......... *A61B 5/0064* (2013.01); *A61B 5/0071* (2013.01); *A61B 5/0075* (2013.01);
(Continued)

(58) Field of Classification Search
CPC ..... A61B 5/1034; A61B 5/1032; A61B 5/443; A61B 5/0064; A61B 5/0205;
(Continued)

(56) References Cited

U.S. PATENT DOCUMENTS 6,452,188 B1 * 9/2002 Chubb ................. A61B 5/0059
250/338.1
6,738,652 B2  5/2004 Mattu et al.
(Continued)

FOREIGN PATENT DOCUMENTS

DE   3137326 A1   3/1983
EP   1726256 A1   11/2006
(Continued)

OTHER PUBLICATIONS

McCamy, Calvin S., H. Marcus, and J. G. Davidson. "A color-rendition chart." J. App. Photog. Eng 2.3 (1976): 95-99.*
(Continued)

*Primary Examiner* — Geoffrey E Summers
(74) *Attorney, Agent, or Firm* — Cooley LLP

(57) ABSTRACT

In medical imaging, a fiducial marker facilitates tissue image correlation that allows for image analysis, normalization and correction of the optical exposure and spectral and spatial distribution in order to compensate for the surface reflections, sub surface tissue interactions and spatial orientation of the excitation and imaging axes to the subject tissue. Using a cross comparison, clinicians can model tissue image data in different forms in order to reference and compare data from various spectral components and or from different images. This may enhance human interpretation between images including the variations between images even when the spectral, spatial and optical conditions or the image resolution or sensitivity are compromised. Such may be used to assess cosmetic, moisturizing, therapeutic materials and treatments.

11 Claims, 8 Drawing Sheets

Related U.S. Application Data

(60) Provisional application No. 61/311,750, filed on Mar. 8, 2010.

(51) Int. Cl.

| | | |
|---|---|---|
| *G03B 15/00* | (2006.01) | |
| *G03B 15/14* | (2006.01) | |
| *A61B 5/0205* | (2006.01) | |
| *A61B 5/026* | (2006.01) | |
| *A61B 5/145* | (2006.01) | |
| *A61B 5/1455* | (2006.01) | |

(52) U.S. Cl.
CPC .......... *A61B 5/0077* (2013.01); *A61B 5/0205* (2013.01); *A61B 5/0261* (2013.01); *A61B 5/1127* (2013.01); *A61B 5/1455* (2013.01); *A61B 5/14546* (2013.01); *A61B 5/14551* (2013.01); *A61B 5/441* (2013.01); *A61B 5/442* (2013.01); *A61B 5/443* (2013.01); *A61B 5/444* (2013.01); *A61B 5/7225* (2013.01); *G03B 15/00* (2013.01); *G03B 15/14* (2013.01); *A61B 5/1128* (2013.01); *A61B 2560/0233* (2013.01)

(58) Field of Classification Search
CPC .............. A61B 5/14551; A61B 5/1455; A61B 5/14546; A61B 5/442; A61B 5/441; A61B 5/444; A61B 5/0077; A61B 5/0075; A61B 5/0071; A61B 5/00261; A61B 5/7225; A61B 5/1128; A61B 5/1127; A61B 2560/0233; G01N 21/293; G03B 15/00; G03B 15/14
USPC ........................................................ 382/167
See application file for complete search history.

(56) References Cited

U.S. PATENT DOCUMENTS

| | | | |
|---|---|---|---|
| 7,162,063 B1 | 1/2007 | Craine et al. | |
| 7,657,101 B2 | 2/2010 | Christiansen et al. | |
| 7,664,298 B2 | 2/2010 | Lang et al. | |
| 8,068,675 B2 | 11/2011 | Christiansen et al. | |
| 9,339,194 B2 | 5/2016 | Adams | |
| 2002/0133080 A1* | 9/2002 | Apruzzese | G01N 21/278 600/477 |
| 2003/0062413 A1 | 4/2003 | Gardiner et al. | |
| 2003/0065278 A1 | 4/2003 | Rubinstenn et al. | |
| 2003/0067545 A1* | 4/2003 | Giron | G03B 15/06 348/223.1 |
| 2004/0218810 A1* | 11/2004 | Momma | A61B 5/0064 382/162 |
| 2004/0240716 A1 | 12/2004 | de Josselin de Jong et al. | |
| 2005/0031176 A1 | 2/2005 | Hertel et al. | |
| 2005/0195316 A1 | 9/2005 | Kollias et al. | |
| 2006/0236586 A1 | 10/2006 | Zaderey | |
| 2007/0058860 A1* | 3/2007 | Harville | G06K 9/00234 382/167 |
| 2007/0086651 A1 | 4/2007 | Stephan et al. | |
| 2008/0008370 A1* | 1/2008 | Chio | A61B 5/441 382/128 |
| 2008/0071162 A1 | 3/2008 | Jaeb et al. | |
| 2008/0103396 A1 | 5/2008 | Johnson et al. | |
| 2008/0214907 A1 | 9/2008 | Gutkowicz-Krusin et al. | |
| 2008/0260218 A1 | 10/2008 | Smith et al. | |
| 2009/0059028 A1* | 3/2009 | Kollias | A61B 5/0071 348/222.1 |
| 2009/0137908 A1 | 5/2009 | Patwardhan | |
| 2009/0166424 A1* | 7/2009 | Gerst | G06K 7/10722 235/462.2 |
| 2009/0201365 A1 | 8/2009 | Fukuoka et al. | |
| 2009/0245603 A1 | 10/2009 | Koruga et al. | |
| 2012/0033867 A1 | 2/2012 | Christiansen et al. | |
| 2013/0096392 A1 | 4/2013 | Adams | |

FOREIGN PATENT DOCUMENTS

| | | | | |
|---|---|---|---|---|
| WO | WO-2006/078902 A2 | 7/2006 | | |
| WO | WO-2007/035597 A2 | 3/2007 | | |
| WO | WO 2007035597 A2 * | 3/2007 | ............ | A61B 5/411 |
| WO | WO-2008/064120 A2 | 5/2008 | | |
| WO | WO-2009/115947 A1 | 9/2009 | | |
| WO | WO-2011/112559 A2 | 9/2011 | | |

OTHER PUBLICATIONS

Na, Renhua, et al. "Autofluorescence spectrum of skin: component bands and body site variations." Skin Research and Technology 6.3 (2000): 112-117.*

Poynton, Charles. "ColorChecker ('Macbeth') Chart." Sep. 11, 2008. Web. Accessed Feb. 16, 2018.*

"Calibration." Academic Press Dictionary of Science and Technology. Oxford: Elsevier Science & Technology, 1992. Credo Reference. Web. Jul. 29, 2014.

"Monotonic, adj." OED Online. Oxford University Press, Jun. 2014. Web. Jul. 31, 2014.

"Monotonicity, n." OED Online. Oxford University Press, Jun. 2014. Web. Jul. 31, 2014.

Mustra, Mario, Kresimir Delac, and Mislav Grgic. "Overview of the DICOM standard." ELMAR, 2008. 50th International Symposium. vol. 1. IEEE, 2008.

Payette, Jeri R., et al. "Assessment of skin flaps using optically based methods for measuring blood flow and oxygenation." Plastic and reconstructive surgery 115.2 (2005): 539-546.

Althof, Raymond J., Marco GJ Wind, and James T. Dobbins. "A rapid and automatic image registration algorithm with subpixel accuracy." Medical Imaging, IEEE Transactions on 16.3 (1997): 308-316.

Treuillet, Sylvie, Benjamin Albouy, and Yves Lucas. "Three-dimensional assessment of skin wounds using a standard digital camera." Medical Imaging, IEEE Transactions on 28.5 (2009): 752-762.

International Search Report and Written Opinion for PCT/US2011/027512, dated Nov. 22, 2011. (ISR and WO cited separately.

International Preliminary Report on Patentability for PCT/US2011/027512, dated Sep. 11, 2012.

Extended European Search Report issued by the European Patent Office for EP Application No. 11753908.0, dated Jul. 29, 2013, five pages.

* cited by examiner

*FIG.6*

SYSTEM, METHOD AND ARTICLE FOR NORMALIZATION AND ENHANCEMENT OF TISSUE IMAGES

CROSS-REFERENCE TO RELATED APPLICATIONS

This application is a continuation of U.S. application Ser. No. 13/583,595, filed Nov. 19, 2012, now issued as U.S. Pat. No. 9,339,194, which is a U.S. national phase entry of International Application No. PCT/US2011/027512, filed Mar. 8, 2011, which application claims the benefit under 35 U.S.C. 119(e) of U.S. provisional patent application Ser. No. 61/311,750, filed Mar. 8, 2010, which are incorporated herein by reference in their entireties.

BACKGROUND OF THE INVENTION

Field of the Invention

The present disclosure relates to the field of medical imaging and in particular to clinical imaging of tissue such as skin or other bodily tissue, with or without lesions, for reference and analysis.

Description of the Related Art

Conventional methods of clinical imaging employ methods where there is little or no control over the light source, exposure, orientation to the subject or the optical characteristics of the image. Images are used to document the visible characteristics of a scene and are used in diverse fields such as remote sensing, dermatology and forensics. In some cases, a measurement tool is introduced into the imaging field of view to allow for approximate correlation of the captured images to a linear scale. In photogrammetry time scale images are compared and corrected for spectral and spatial frequency distributions. This is often a laborious process. Spectral artifacts are difficult to correlate in a time series of digital images due to variation in angles of the source light and variation in optical axes and the impacts of ambient conditions. Photogrammetric observations use tracking of parameters such as position, distance from the subject and time, to ensure the optical angles of reference can be used in image correlation and rectification. Rectification is often complicated by the three dimensional characteristics of the scene. In medical imaging, coordinate systems can be used to spatially relate subject matter to a standard, such as the Talairach atlas.

Applicant is not aware of any standard by which photographic or spectroscopic images of human tissue can be used to repeatedly establish the tissue specific molecular optical characteristics of all subjects at different times, with different optical conditions. U.S. Pat. No. 6,738,652 discusses the optical thickness of the skin as a ratio of protein to fat spectra. The correlation of an image time series using conventional techniques is complicated by the inability to accurately compensate for exact changes due to variations in the ambient conditions.

Therefore there is a need for technical approaches in clinical imaging that allow clinicians to quickly acquire skin images without having to concern themselves with the complex optical considerations that surround the rectification and registration of images.

This background information is provided to reveal information believed by the applicant to be of possible relevance to the present application. No admission is necessarily intended, nor should be construed, that any of the preceding information constitutes prior art against the present application.

BRIEF SUMMARY

Systems, methods and articles allow correction of tissue images corresponding to spectral effects in a tissue sample due to the complex interactions of light and where a computer model of tissue image data may be used to cross reference and compare data from various spatial and spectral components and or from different images, to model lesion shape.

Systems, method and articles allow correction and analysis of a digital image in three dimensions, where physical and/or virtual fiducial markers are used in the imager field of view, and where the fiducial marker is of a form that includes a well defined shape and color variations and where some of the color areas on the fiducial marker are used as optical phantoms to match the spectral character of living tissue including a reflective layer to simulate the optical character of the skin.

A system and a method may be summarized as performing correction and analysis of digital images in three dimensions in which a fiducial marker appears, the fiducial marker having a well defined shape and color variations, where some of the color areas on the fiducial marker are optical phantoms to match the spectral character of living tissue and have a reflective layer to simulate an optical character of living bodily tissue such as skin.

The correction may correspond to a set of spectral effects of the tissue sample, which arise due to complex interactions of light. A computer or digital model of tissue image data may be used by the system or method to cross reference and compare data from various spatial and spectral components and/or from different images, to model lesion shape. The analysis comparison of layers may take the form of a histogram.

The system or method may use the optical spectral data from the digital image to create a three dimensional digital reconstruction of the lesion, including multispectral data and image timeline data.

The optical phantom can be related to the individual spectral components of skin with layers. The system or method may normalize a multiple image series. The optical phantom may include an Epidermal Layer Phantom in the visible spectrum of 500 nm to 600 nm; a Melanin Layer Phantom in the spectrum of 300 nm to 500 nm; a Hemoglobin Layer Phantom where oxyhemoglobin absorption peaks close to 415 nm, 515 nm, 590 nm or where in contrast deoxyhemoglobin peaks at 430 nm, 575 nm, 610 nm; a Collagen Layer Phantom where absorption is between 340 nm to 400 nm with a fluorescence peak between 450 nm to 550 nm (the fluorescent peak may be created with fluorescein or 5-carboxyfluorescein), a water phantom where absorption peaks in the range of 450 nm; 575 nm; 630 nm; 730 nm; 820 nm, or in contrast reflection peaks at 514 nm; 606 nm; 660 nm; 739 nm.

A system and method for correction and analysis of digital images in three dimensions, may employ one or more fiducial markers, which are physically placed or optically projected into the image field of view, and where the fiducial marker is of a form that includes a well defined shape and color variations and where some of the color areas on the fiducial marker that are used as optical phantoms to match the spectral character of living tissue also have a reflective layer to simulate the optical character of the skin.

A digital image time series is normalized using numerical methods, for example by measuring the difference of the spectral distribution between the optical character of the tissue in combination with the fiducial marker where the monotonicity of certain spectral relationships may be outside or approaching the limit of the normal spectral distribution. Normal may be determined by the optical character of a subjects' healthy tissue or in comparison to a population. A digital image may be normalized to the fiducial marker, yet require to be normalized based on the spectral markers such those of hemoglobin and collagen. A normalization of optical relationships may result in an analysis including generation of a probability distribution of a tissue being abnormal. The abnormal relationship may be represented by an optical density compared to a percentage of optical spectra that can be attributed to that of collagen. An abnormal relationship represented in the digital images may be viewed within an assigned probability index, that allows certain digital images to be weighted by their diagnostic value or weighted by comparative changes between spectra, which may show or be indicative of a trend. The optical properties of hemoglobin, collagen, melanin and/or epidermis may be used as an optical signature representative of tissue or of a specific individual person.

Correction for correlation of digital images may also include color correction information in order to establish lesion border parameters that might include fluorescence and reflection changes, or by comparison of the surface optical spectra to the subsurface spectra. A multidimensional lesion map can be made to track the pixel characteristics in the digital image such as surface, sub-surface and other layers or depth characteristics as may be determined from the spectral analysis, such as areas of molecular activity, blood flow or tissue density. Variation between image layer coordinates in a time series of digital images may be used for registration and a standardized method of optical correlation.

The optical or spectral data may be combined with spatial data to create true three dimensional digital models of the lesions including growth comparisons, and where the shape of the tissue is rectified with a three dimensional topographic map of the body that combines three dimensional model probabilities, with correlation of coordinate locations and spectral effects and complex interactions.

The normalized images enable clinicians through automated updates, to be able to make diagnostic decisions using a standard protocol. The system and method may also be used to establish a baseline optical/molecular index for an individual patient and this data used to contribute to the normalization of images or be used in a timeline as a diagnostic test. In particular, the digital images may be analyzed and a probability index created from the combination of distributed properties of the variables including normalization, exposure correction, geometric correlation, optical spectroscopic correction, signal to noise characterization and diagnostic protocols.

A method of operating a system for use in tissue analysis may be summarized as including comparing by at least one processor an appearance of at least one shape of at least a first fiducial marker in a first digital image of a portion of a tissue to at least one defined actual shape of the fiducial marker; comparing by the at least one processor an appearance of each of a plurality of sections of the fiducial marker in the first digital image to respective ones of defined sections of the fiducial marker including a number of tissue phantoms each having a respective spectral characteristic that matches a respective spectral characteristic of tissue of a type represented in the first digital image; and at least one of correlating, normalizing, or correcting at least the first digital image, based at least in part on the comparisons. The fiducial marker may include a scatter layer that overlies at least some of the tissue phantoms and which simulates an optical character of the type of tissue represented in the first digital image, and wherein comparing an appearance of each of a plurality of sections of the fiducial marker in the first digital image to respective ones of defined sections of the fiducial marker includes comparing the appearance of the sections which include the tissue phantoms which are overlaid by the scatter layer with a number of defined sections which include the tissue phantoms overlaid by the scatter layer. A number of sections of the fiducial marker may include a respective color including at least one of black, white, a plurality of different shades of grey, and a plurality of additional colors that are not black, white or grey, and wherein comparing an appearance of each of a plurality of sections of the fiducial marker in the first digital image to respective ones of defined sections of the fiducial marker includes comparing the appearance of the sections which include the respective colors with respective ones of a defined set of respective colors.

The method may further include storing to at least one nontransitory storage medium the digital image as a multilayer image file, including a first digital image layer that stores and at least a second digital image layer that stores image metadata.

The method may further include storing to a diagnostic layer of the digital image on the nontransitory storage medium information indicative of at least one of an NADH fluorescence, a collagen fluorescence, a physical scattering of light from the tissue at a number of physical layers of the tissue due to tissue density, a spectral distribution due to a size of a cell nuclei, and a hemoglobin absorption due to increased blood flow or oxygenation.

The method may further include registering a number of subsequent digital images in spatial and optical relationship by the at least one processor; and comparing the first and the subsequent digital images on a layer by layer basis by the at least one processor.

The system may further include referencing by the at least one processor at least one of spectral changes or optical density at specific coordinates in the first digital image to allow later comparison to changes in a number of subsequent digital images of the region of interest.

The method may further include comparing by the at least one processor a number of ratios of respective radiant spectral intensity of a number of wavelengths or wavebands in the first digital image.

The method may further include comparing by the at least one processor a number of ratios of respective radiant spectral intensity of a number of wavelengths or wavebands in at least one subsequent digital image. Normalizing may include normalizing a plurality of digital images including the first digital image by measuring a difference of a spectral distribution between an optical character of the tissue in combination with the fiducial marker, where a monotonicity of a number of defined spectral relationships is proximate or exceeds a limit of a normal spectral distribution.

The method may further include establishing a subject specific baseline by the at least one processor which is specific to an individual; and wherein the normalizing is based at least in part on the subject specific baseline the first digital image and a plurality of sequential digital images, the sequential digital images sequentially captured at various times following a capture of the first digital image.

The method may further include determining a number of differences in the region of interest as the region of interest appears between the normalized digital images including the first digital image and the plurality of sequential digital images, by the at least one processor, as part of a tissue analysis. Determining a number of differences may include determining any morphological changes of the region of interest as the region of interest appears between the digital images as part of the determination of the differences in the region of interest as the region of interest appears between the normalized digital images including the first digital image and the plurality of sequential digital images. Determining a number of differences may include assessing any change in at least one of a level of skin hydration, a total number of wrinkles or a size of at least one wrinkle, or a total number of blemishes or a size of at least one blemish. Determining a number of differences may include assessing at least one of a level of hydration or a level of blood flow between the first digital image and at least one subsequent digital image, where the first digital image represents the region of interest prior to a first application of a cosmetic, a moisturizer, a therapeutic or a therapeutic treatment and the at least one subsequent digital mage represents the region of interest after the first application of the cosmetic, the moisturizer, the therapeutic or the therapeutic treatment. Normalizing may include normalizing at least the first digital image based at least in part on a spectral marker of hemoglobin and a spectral marker of collagen.

The system may further include generating a probability index by the at least one processor based on a combination of distributed properties of a number of variables including a normalization, an exposure correction, a geometric correlation, an optical spectroscopic correction, a signal to noise characterization, or a defined diagnostic protocol. The instructions may further cause the at least one processor to generate a digital model that geometrically represents the region of interest in three dimensions based on spatial and spectral data from the digital images.

The method may further include associating at least one of multispectral data or image timeline data to the digital model that geometrically represents the region of interest in three dimensions by the at least one processor.

The method may further include rectifying the tissue by the at least one processor with a three dimensional map of at least a portion of a body which combines a set of three dimensional model probabilities with a correlation of a set of coordinate locations, a set of spectral effects and a set of complex interactions. Correcting may include correcting at least the first digital image based at least in part on color correction information.

The method may further include generating by the at least one processor a digital multidimensional lesion map that tracks a set of pixel characteristics in at least the first digital image including at least one of a surface, a sub-surface, other layers or a depth characteristic of the tissue as determined from a spectral analysis of the tissue as represented in at least the first digital image.

Correcting may further include correcting for spectral effects in the tissue represented in at least the first digital image which spectral effects are due to interactions of light absorption, reflectance and fluorescence, and to cross reference and compare a number of spatial and a number of spectral components specified by at least one of a digital model of tissue image data or another digital image to generate the digital three dimensional model of the region of interest. Correcting may include correcting for differences in spatial orientation of at least one of an excitation axis or an imaging axis of a tissue imaging system in Cartesian space.

The method may further include registering each of a plurality of digital images of the tissue by the at least one processor, including the first digital image, based at least in part on a variation between image layer coordinates in a temporal sequence of a plurality of digital images of the tissue.

The method may further include generating by the at least one processor an analysis comparison of layers in at least the first digital image as a histogram.

The method may further include generating by the at least one processor a probability distribution of a tissue being abnormal. Generating a probability distribution of a tissue being abnormal may include generating the probability distribution of the tissue being abnormal based at least in part on a comparison of an optical density to a percentage of optical spectra that is attributable to collagen. A probability distribution of a tissue being abnormal may include generating the probability distribution with a probability index that weights at least some digital images according to at least one of a diagnostic value or a comparative amount of change between spectra.

A system for use in tissue analysis may be summarized as including at least one processor; and at least one nontransitory storage medium that stores processor executable instructions which when executed cause the at least one processor to: compare an appearance of at least one shape of at least a first fiducial marker in a first digital image of a portion of a tissue to at least one defined actual shape of the fiducial marker; compare an appearance of each of a plurality of sections of the fiducial marker in the first digital image to respective ones of defined sections of the fiducial marker including a number of tissue phantoms each having a respective spectral characteristic that matches a respective spectral characteristic of tissue of a type represented in the first digital image; and at least one of correlate, normalize, or correct at least the first digital image, based at least in part on the comparisons. The fiducial marker may include a scatter layer that overlies at least some of the tissue phantoms and which simulates an optical character of the type of tissue represented in the first digital image, and the instructions cause the at least one processor to compare the appearance of the sections which include the tissue phantoms which are overlaid by the scatter layer with a number of defined sections which include the tissue phantoms overlaid by the scatter layer. A number of sections of the fiducial marker may include a respective color including at least one of black, white, a plurality of different shades of grey, and a plurality of additional colors that are not black, white or grey, and the instructions cause the at least one processor to compare the appearance of the sections which include the respective colors with respective ones of a defined set of respective colors.

The instructions may further cause the at least one processor to store the digital image as a multi-layer image file, including a first digital image layer that stores and at least a second digital image layer that stores image metadata.

The instructions may further cause the at least one processor to store to a diagnostic layer of the digital image information indicative of at least one of an NADH fluorescence, a collagen fluorescence, a physical scattering of light from the tissue at a number of physical layers of the tissue due to tissue density, a spectral distribution due to a size of a cell nuclei, and a hemoglobin absorption due to increased blood flow or oxygenation.

The instructions may further cause the at least one processor to register a number of subsequent digital images in spatial and optical relationship and to compare the first and the subsequent digital images on a layer by layer basis.

The instructions may further cause the at least one processor to reference at least one of spectral changes or optical density at specific coordinates in the first digital image to allow later comparison to changes in a number of subsequent digital images of the region of interest.

The instructions may further cause the at least one processor to compare a number of ratios of respective radiant spectral intensity of a number of wavelengths or wavebands in the first digital image.

The instructions may further cause the at least one processor to compare the number of ratios of respective radiant spectral intensity of the number of wavelengths or wavebands in the first digital image to a number of ratios of a respective radiant spectral intensity of a number of wavelengths or wavebands in at least one subsequent digital image.

The instructions may further cause the at least one processor to normalize a plurality of digital images including the first digital image by measuring a difference of a spectral distribution between an optical character of the tissue in combination with the fiducial marker, where a monotonicity of a number of defined spectral relationships is proximate or exceeds a limit of a normal spectral distribution.

The instructions may further cause the at least one processor to establish a subject specific baseline which is specific to an individual, and normalize based at least in part on the subject specific baseline the first digital image and a plurality of sequential digital images, the sequential digital images sequentially captured at various times following a capture of the first digital image.

The instructions may further cause the at least one processor to determine differences in the region of interest as the region of interest appears between the normalized digital images including the first digital image and the plurality of sequential digital images as part of a analysis.

The instructions may further cause the at least one processor to determine morphological changes of the region of interest as the region of interest appears between the digital images as part of the determination of the differences in the region of interest as the region of interest appears between the normalized digital images including the first digital image and the plurality of sequential digital images. The instructions may cause the at least one processor to determine the number of differences by assessing any change in at least one of a level of skin hydration, a total number of wrinkles or a size of at least one wrinkle, or a total number of blemishes or a size of at least one blemish. The instructions may cause the at least one processor to determine the number of differences by assessing at least one of a level of hydration or a level of blood flow between the first digital image and at least one subsequent digital image, where the first digital image represents the region of interest prior to a first application of a cosmetic, a moisturizer, a therapeutic or a therapeutic treatment and the at least one subsequent digital mage represents the region of interest after the first application of the cosmetic, the moisturizer, the therapeutic or the therapeutic treatment.

The instructions may further cause the at least one processor to normalize at least the first digital images] based at least in part on a spectral marker of hemoglobin and a spectral marker of collagen.

The instructions may further cause the at least one processor to generate a probability index based on a combination of distributed properties of a number of variables including a normalization, an exposure correction, a geometric correlation, an optical spectroscopic correction, a signal to noise characterization, or a defined diagnostic protocol.

The instructions may further cause the at least one processor to generate a digital model that geometrically represents the region of interest in three dimensions based on spatial and spectral data from the digital images.

The instructions may further cause the at least one processor to associate at least one of multispectral data or image timeline data to the digital model that geometrically represents the region of interest in three dimension The instructions may further cause the at least one processor to rectify the tissue with a three dimensional map of at least a portion of a body which combines a set of three dimensional model probabilities with a correlation of a set of coordinate locations, a set of spectral effects and a set of complex interactions.

The instructions may further cause the at least one processor to correct at least the first digital image based at least in part on color correction information.

The instructions may further cause the at least one processor to generate a digital multidimensional lesion map that tracks a set of pixel characteristics in at least the first digital image including at least one of a surface, a sub-surface, other layers or a depth characteristic of the tissue as determined from a spectral analysis of the tissue as represented in at least the first digital image.

The instructions may further cause the at least one processor to correct for spectral effects in the tissue represented in at least the first digital image which spectral effects are due to interactions of light absorption, reflectance and fluorescence, and to cross reference and compare a number of spatial and a number of spectral components specified by at least one of a digital model of tissue image data or another digital image to generate the digital three dimensional model of the region of interest.

The instructions may further cause the at least one processor to correct for differences in spatial orientation of at least one of an excitation axis or an imaging axis of a tissue imaging system in Cartesian space.

The instructions may further cause the at least one processor to perform a registration on each of a plurality of digital images of the tissue, including the first digital image, based at least in part on a variation between image layer coordinates in a temporal sequence of a plurality of digital images of the tissue.

The instructions may further cause the at least one processor to generate an analysis comparison of layers in at least the first digital image as a histogram.

The instructions may further cause the at least one processor to generate a probability distribution of a tissue being abnormal.

The instructions may further cause the at least one processor to generate the probability distribution of the tissue being abnormal based at least in part on a comparison of an optical density to a percentage of optical spectra that is attributable to collagen.

The instructions may further cause the at least one processor to generate the abnormal relationship of the images are viewed within a probability index that weights at least some digital images according to at least one of a diagnostic value or a comparative amount of change between spectra.

A fiducial marker for use in tissue imaging may be summarized as including a substrate having a defined profile and bearing a plurality of sections having respective wavelength selective absorption, reflectance or florescence characteristic, at least a first number of the sections form a color chart of a plurality of different colors and at least a second number of the sections are optical phantoms that match respective ones of a number of spectral characteristics of living tissue.

The fiducial marker may further include a scattering layer overlying at least a first set of the sections. The scattering layer may have a number of characteristics that simulate a number of optical characteristics of at least one layer of the living tissue. The optical characteristics may be those of skin. The second number of the sections may include at least one of a first section having a selective spectral absorption at a waveband of about 330 nm to about 500 nm, a second section having a selective spectral absorption at a wavelength at about 415 nm, about 515 nm, or about 590 nm, a third section having a selective spectral absorption at a waveband of about 340 nm to about 400 nm, a fourth section having a selective spectral fluorescence at a waveband of about 450 nm to about 550 nm, or a fifth section having a selective spectral absorption at about 550 nm, about 630 nm, about 730 nm, or about 820 nm or a reflection peak at about 514 nm, about 606 nm or about 739 nm. The fourth section may include at least one of fluorescein or 5-carboxyfluorescein. The second number of the sections may include each of a melanin layer phantom section having a selective spectral absorption at a waveband of about 330 nm to about 500 nm, a hemoglobin layer phantom section having a selective spectral absorption at a wavelength at approximately 415 nm, about 515 nm, or about 590 nm, a first collagen layer phantom section having a selective spectral absorption at a waveband of about 340 nm to about 400 nm, a second collagen layer phantom section having a spectral fluorescence at a waveband of about 450 nm to about 550 nm, and a fifth section having a selective spectral absorption at about 550 nm, about 630 nm, about 730 nm, or about 820 nm or a reflection peak at about 514 nm, about 606 nm or about 739 nm. At least a second set of the sections may not be overlaid by the scattering layer. The colors in the color chart may include at least one of black or white. The colors in the color chart may include a plurality of different shades of grey. A first set of the sections may include a first color chart having a black section, a white section, a plurality of sections each of which is a respective shade of grey and a plurality of sections each of which is a respective one of a plurality of additional colors, all the sections of the first set overlaid by a scattering layer, and a second set of the sections includes a second color chart having a black section, a white section, a plurality of sections each of which is a respective shade of grey and a plurality of sections each of which is a respective one of a plurality of additional colors, none of the sections of the second set overlaid by a scattering layer. The defined profile may be a polygon.

A system to image bodily tissues may be summarized as including a physical fiducial marker selectively positionable at least proximate a region of interest on a portion of a bodily tissue to be imaged, the physical fiducial marker including a substrate having a defined profile and bearing a plurality of sections having respective wavelength selective absorption, reflectance or florescence characteristic, at least a first number of the sections form a color chart of a plurality of different colors and at least a second number of the sections are optical phantoms that match respective ones of a number of spectral characteristics of living tissue; at least one light source operable to project a virtual fiducial marker at least proximate the region of interest on the portion of the bodily tissue to be imaged, the virtual fiducial marker having a defined profile and a plurality of defined shapes; and an image capture device having a field of view and configured to capture digital images of bodily tissue including the region of interest, the physical fiducial marker and the virtual fiducial marker all encompassed by the field of view of the image capture device. The virtual fiducial marker may be projected with the plurality of defined shapes as straight line segments. The virtual fiducial marker may be projected with the profile of a circle and with the plurality of defined shapes as straight line segments emanating from a center point of the circular profile. The defined profile of the physical fiducial marker may be a polygon. The colors in the color chart may include at least one of black, white, a plurality of different shades of grey, a plurality of additional colors that are not black, white or grey.

A method of operating a system for use in tissue analysis may be summarized as including assessing by at least one processor of the system a change in at least one of a level of hydration, a level of blood flow, a total number of wrinkles, a size of at least one wrinkle, a total number of blemishes, or a size of at least one blemish between a first digital image of a region of interest of a bodily tissue and at least one subsequent digital image of the region of interest of the bodily tissue, where the first digital image represents the region of interest prior to a first application of a cosmetic, a moisturizer, a therapeutic or a therapeutic treatment and the at least one subsequent digital mage represents the region of interest after the first application of the cosmetic, the moisturizer, the therapeutic or the therapeutic treatment; and reporting by the at least one processor of the system the assessed difference in a visual form. Assessing a change in at least one of a level of hydration, a level of blood flow, a total number of wrinkles, a size of at least one wrinkle, a total number of blemishes, or a size of at least one blemish between a first digital image of a region of interest of a bodily tissue and at least one subsequent digital image of the region of interest of the bodily tissue may include assessing a number of spectral characteristics of the region of interest in the first and the at least one subsequent digital image. Assessing a number of spectral characteristics of the region of interest in the first and the at least one subsequent digital image may include assessing a spectral absorption, reflectance or fluorescence response of a number of layers of skin characteristic of water, hemoglobin, and collagen.

The method may further include comparing by the at least one processor of the system an appearance of at least one shape of at least a first fiducial marker in a first digital image of a portion of a tissue to at least one defined actual shape of the fiducial marker; comparing by the at least one processor of the system an appearance of each of a plurality of sections of the fiducial marker in the first digital image to respective ones of defined sections of the fiducial marker including a number of tissue phantoms each having a respective spectral characteristic that matches a respective spectral characteristic of tissue of a type represented in the first digital image; and at least one of correlating, normalizing, or correcting at least the first digital image based at least in part on the comparisons. The assessing may be performed after the at least one of correlating, normalizing, or correcting at least the first digital image based at least in part on the comparisons.

A system for use in tissue analysis may be summarized as including at least one processor; and at least one nontransitory storage medium that stores processor executable instructions which when executed cause the at least one processor to: assess a change in at least one of a level of hydration, a level of blood flow, a total number of wrinkles, a size of at least one wrinkle, a total number of blemishes, or a size of at least one blemish between a first digital image of a region of interest of a bodily tissue and at least one subsequent digital image of the region of interest of the bodily tissue, where the first digital image represents the region of interest prior to a first application of a cosmetic, a moisturizer, a therapeutic or a therapeutic treatment and the at least one subsequent digital mage represents the region of interest after the first application of the cosmetic, the moisturizer, the therapeutic or the therapeutic treatment; and report the assessed difference in a visual form. The instructions may cause the at least one processor to assess a change in at least one of a level of hydration, a level of blood flow, a total number of wrinkles, a size of at least one wrinkle, a total number of blemishes, or a size of at least one blemish between a first digital image of a region of interest of a bodily tissue and at least one subsequent digital image of the region of interest of the bodily tissue by assessing a number of spectral characteristics of the region of interest in the first and the at least one subsequent digital image. The instructions may cause the at least one processor to assess a number of spectral characteristics of the region of interest in the first and the at least one subsequent digital image by determining a spectral absorption, reflectance or fluorescence response of a number of layers of skin characteristic of water, hemoglobin, and collagen. The instructions may cause the at least one processor to: compare an appearance of at least one shape of at least a first fiducial marker in a first digital image of a portion of a tissue to at least one defined actual shape of the fiducial marker; compare an appearance of each of a plurality of sections of the fiducial marker in the first digital image to respective ones of defined sections of the fiducial marker including a number of tissue phantoms each having a respective spectral characteristic that matches a respective spectral characteristic of tissue of a type represented in the first digital image; and at least one of correlate, normalize, or correct at least the first digital image based at least in part on the comparisons. The at least one processor may perform the assessing after performing the at least one of correlation, normalization, or correction of at least the first digital image based at least in part on the comparisons. The at least one processor performs may includes a therapy recommendation in the report based on the assessment.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements and angles are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 6 is a top plan view of a fiducial marker, according to one illustrated embodiment, which illustrates color sectors of the fiducial marker; (a, b, c, d, e, f) being the primary and secondary reference colors; (g, h) being the skin pigment reference colors; (i, j, k, l) being the black, white and grey scale; and (m, n, o, p) being the optical phantom reference sections of the tissue optical layers.

DETAILED DESCRIPTION

Figure 1:
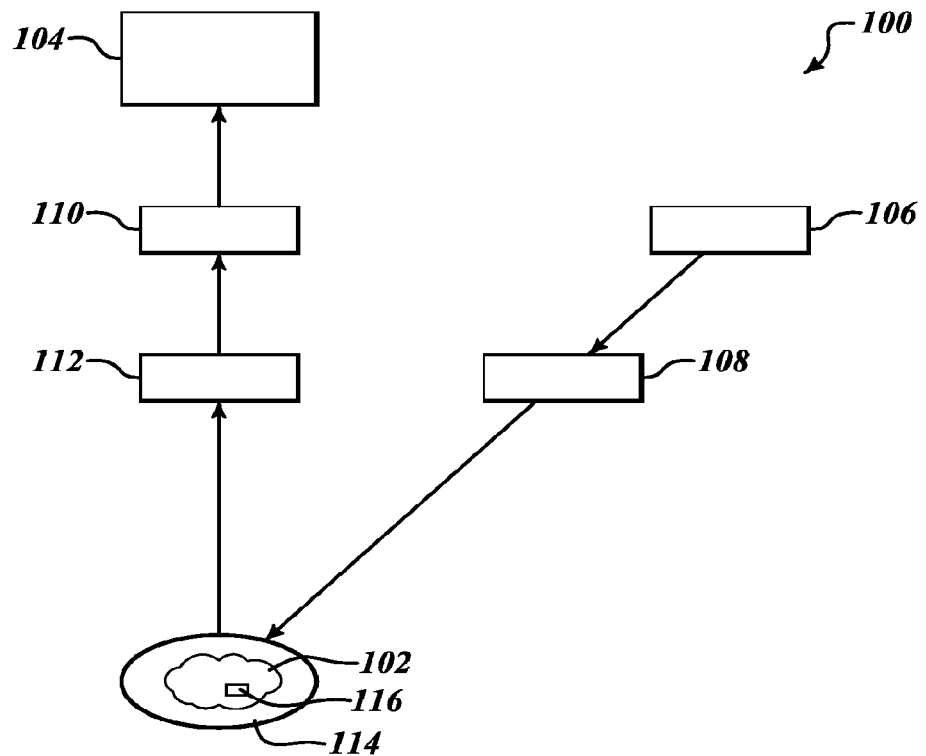
FIG. 1 is a schematic diagram that illustrates a tissue imaging system and a subject tissue, showing an orientation of the imaging to the subject tissue, according to one illustrated embodiment.

In the following description, certain specific details are set forth in order to provide a thorough understanding of various embodiments of the invention. However, one skilled in the art will understand that the invention may be practiced without these details. In other instances, well-known structures associated with cameras, imagers, scanners, optics, computers, computer networks, data structures, databases, and networks such as the Internet or cellular networks, have not been described in detail to avoid unnecessarily obscuring the descriptions of the embodiments of the invention.

Unless the context requires otherwise, throughout the specification and claims which follow, the word "comprise" and variations thereof, such as "comprises" and "comprising" are to be construed in an open, inclusive sense, that is as "including but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the claimed invention.

As used herein and in the claims, "spectral effects" means the absorption, reflection, exposure levels, white balance and fluorescence and variations for optical conditions such as chromatic aberrations and focus, and spherical aberrations and spatial corrections such as three dimensional characteristics and the orientation of the tissue imaging system in Cartesian space.

As used herein and in the claims, "complex interactions" means the interaction of light in the various types of tissue due to tissue layers, spectral effects where a subject image is transformed into a coordinate system and imaging conditions are the result of the relationship between various optical spectra and the tissue of interest.

As used herein and in the claims, "lesion shape" means the three dimensional shape, volume and/or depth of infiltration of a skin lesion including compensation for spectral effects and complex interactions, where digital images or digital photographs can be normalized using a fiducial marker via computer image processing methods.

As used herein and in the claims, "analysis or diagnosis" means the resulting comparison of differences from one portion of an image to another portion of the image, or from one image to another image. A static or timeline image sequence can be used by clinicians to evaluate the significance of any changes due to the propagation and attenuation of light of certain defined wavelengths and for the different physical layers of the skin, and data regarding the spectral distribution of the reflected and the back scattered light including compensation for lesion shape, spectral effects and complex interactions.

As used herein and in the claims, "fiducial marker" means a system for correcting for the variations in spectral power distribution from one image to another including a fiducial marker color chart with a physical arrangement of known colors and used for color registration within the image space including calibration of the reflected light from the subject including comparing and adjusting with the color chart including the white balance and grey scale and where a tissue phantom on the fiducial marker is used for correlation of light from deeper tissue and to minimize the effect from surface reflection.

As used herein and in the claims, the term "about" refers to a +/−10% variation from the nominal value. It is to be understood that such a variation is always included in a given value provided herein, whether or not it is specifically referred to.

Unless defined otherwise, all technical and scientific terms used herein have the same meaning as commonly understood by one of ordinary skill in the art to which this application relates.

Overview

FIG. 1 shows a tissue imaging system 100 according to one illustrated embodiment, which may be used to capture images of tissue 102 for analysis and diagnosis.

The tissue imaging system 100 includes a digital camera 104 or other image capture device operable to capture images of tissue 102. One example of a professional digital camera that may be suitable is an Alta U series digital camera commercially available from Apogee Instruments. Alternatively, a consumer style camera may be suitable, for example an SD 1300 digital camera commercially available from Canon.

The tissue imaging system 100 may include one or more excitation sources 106, which may, or may not, be integral to the digital camera 104. Suitable excitation sources 106 may include a xenon flash tube or bulb and associated circuitry. The tissue imaging system 100 may include one or more excitation filters 108 positioned between the excitation source(s) 106 and the tissue 102 to filter electromagnetic radiation emitted by the excitation source(s) 106.

The tissue imaging system 100 may include one or more imaging lenses 110. The imaging lenses 110 may, or may not, be integral to the digital camera 104. The imaging lenses 110 may be used to adjust a focal point and/or depth of field of the tissue imaging system 100. The tissue imaging system 100 may include one or more imaging filters 112 positioned between the tissue 102 and the imaging lenses 110 or digital camera 104 to filter electromagnetic radiation returned (e.g., reflected, emitted) by the tissue 102. Within the image field of view 114 of the digital camera 104 is placed a fiducial marker 116 which facilitates normalization between digital images.

Figure 2:
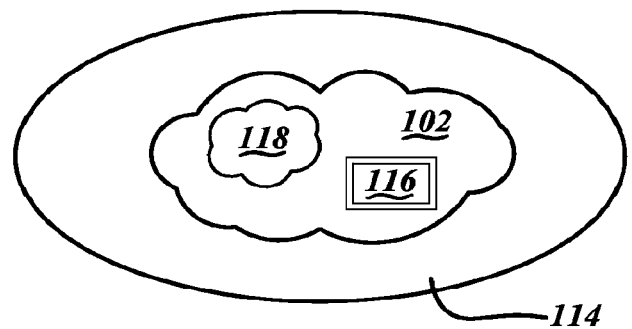
FIG. 2 is a schematic diagram that illustrates a field of view which encompasses a subject tissue, including an area of interest and a fiducial marker, showing a spatial context of the subject components and the fiducial marker within the field of view or relative to the area of interest (x, y), according to one illustrated embodiment.

FIG. 2 shows the field of view 116 of the digital camera 104 (FIG. 1), according to one illustrated embodiment.

The field of view 114 encompasses a portion of tissue 102, which includes a region of interest 118. The region of interest 118 may take the form of a lesion, growth or some other structure of, or on, the tissue 102. The field of view 114 also encompasses the fiducial marker 116.

Figure 3:
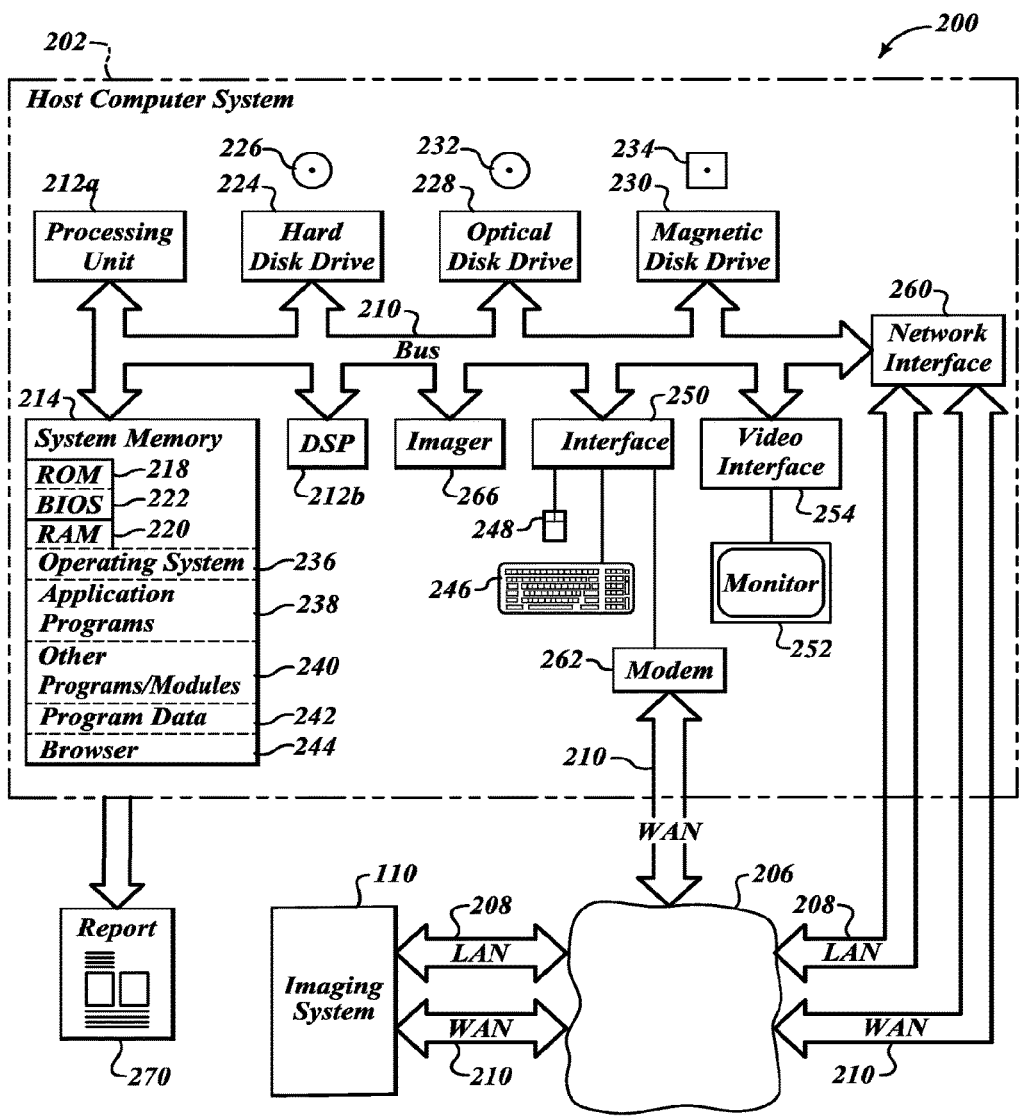
FIG. 3 is a schematic diagram of an tissue imaging system and tissue image processing host computing system, remotely located from and communicatively coupled to the tissue imaging system, according to one illustrated embodiment.

FIG. 3 shows a tissue imaging and digital image processing system 200 according to one illustrated embodiment.

The tissue imaging and digital image processing system 200 includes one or more tissue imaging systems 100, for example identical or similar to the tissue imaging system 100 discussed in reference to FIGS. 1 and 2. The tissue imaging and digital image processing system 200 also includes one or more tissue image processing host computer systems 202. The tissue imaging system(s) 100 is(are) communicatively coupled to the tissue image processing host computer system(s) 202 by one or more communications channels, for example the Internet 206, one or more local area networks (LANs) 208 or wide area networks (WANs) 210. The tissue image processing host computer system 202 will at times be referred to in the singular herein, but this is not intended to limit the embodiments to a single device since in typical embodiments, there may be more than one clinic, hospital, or image processing service or facility involved. Unless described otherwise, the construction and operation of the various blocks shown in FIG. 2 are of conventional design. As a result, such blocks need not be described in further detail herein, as they will be understood by those skilled in the relevant art.

The tissue image processing host computer system 202 may take the form of a conventional mainframe computer, mini-computer, workstation computer, personal computer (desktop or laptop), or handheld computer. Non-limiting examples of commercially available computer systems include, but are not limited to, an 80×86 or Pentium series microprocessor from Intel Corporation, U.S.A., a PowerPC microprocessor from IBM, a Sparc microprocessor from Sun Microsystems, Inc., a PA-RISC series microprocessor from Hewlett-Packard Company, or a 68xxx series microprocessor from Motorola Corporation.

The tissue image processing host computer system 202 may include one or more processing units 212a, 212b (collectively 212), a system memory 214 and a system bus 216 that couples various system components including the system memory 214 to the processing units 212. The processing units 212 may be any logic processing unit, such as one or more central processing units (CPUs) 212a, digital signal processors (DSPs) 212b, application-specific integrated circuits (ASICs), field programmable gate arrays (FPGAs), etc. The system bus 216 can employ any known bus structures or architectures, including a memory bus with memory controller, a peripheral bus, and a local bus. The system memory 214 includes read-only memory ("ROM") 218 and random access memory ("RAM") 220. A basic input/output system ("BIOS") 222, which can form part of the ROM 218, contains basic routines that help transfer information between elements within the tissue image processing host computer system 202, such as during start-up.

The tissue image processing host computer system 202 may include a hard disk drive 224 for reading from and writing to a hard disk 226, an optical disk drive 228 for reading from and writing to removable optical disks 232, and/or a magnetic disk drive 230 for reading from and writing to magnetic disks 234. The optical disk 232 can be a CD-ROM, while the magnetic disk 234 can be a magnetic floppy disk or diskette. The hard disk drive 224, optical disk drive 228 and magnetic disk drive 230 may communicate with the processing unit 212 via the system bus 216. The hard disk drive 224, optical disk drive 228 and magnetic disk drive 230 may include interfaces or controllers (not shown) coupled between such drives and the system bus 216, as is known by those skilled in the relevant art. The drives 224, 228 and 230, and their associated computer-readable storage media 226, 232, 234, may provide nonvolatile and non-transitory storage of computer readable instructions, data structures, program modules and other data for the tissue image processing host computer system 202. Although the depicted tissue image processing host computer system 202 is illustrated employing a hard disk 224, optical disk 228 and magnetic disk 230, those skilled in the relevant art will appreciate that other types of computer-readable storage media that can store data accessible by a computer may be employed, such as magnetic cassettes, flash memory, digital video disks ("DVD"), Bernoulli cartridges, RAMs, ROMs, smart cards, etc.

Program modules can be stored in the system memory 214, such as an operating system 236, one or more application programs 238, other programs or modules 240 and program data 242. Application programs 238 may include instructions that cause the processor(s) 212 to automatically normalize digital images or information therefrom based on fiducial markers in those digital images and/or compare tissue or lesions between normalized digital images. Other program modules 240 may include instructions for handling security such as password or other access protection and communications encryption. The system memory 214 may also include communications programs for example a Web client or browser 244 for permitting the tissue image processing host computer system 202 to access and exchange data with sources such as Web sites of the Internet, corporate intranets, extranets, or other networks as described below, as well as other server applications on server computing systems such as those discussed further herein. The browser 244 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document. A number of Web clients or browsers are commercially available such as those from Mozilla, Google and Microsoft of Redmond, Wash.

While shown in FIG. 2 as being stored in the system memory 214, the operating system 236, application programs 238, other programs/modules 240, program data 242 and browser 244 can be stored on the hard disk 226 of the hard disk drive 224, the optical disk 232 of the optical disk drive 228 and/or the magnetic disk 234 of the magnetic disk drive 230.

An operator can enter commands and information into the tissue image processing host computer system 202 through input devices such as a touch screen or keyboard 246 and/or a pointing device such as a mouse 248, and/or via a graphical user interface. Other input devices can include a microphone, joystick, game pad, tablet, scanner, etc. These and other input devices are connected to one or more of the processing units 212 through an interface 250 such as a serial port interface that couples to the system bus 216, although other interfaces such as a parallel port, a game port or a wireless interface or a universal serial bus ("USB") can be used. A monitor 252 or other display device is coupled to the system bus 216 via a video interface 254, such as a video adapter. The host computer system tissue image processing can include other output devices, such as speakers, printers, etc.

The tissue image processing host computer system 202 can operate in a networked environment using logical connections to one or more remote computers and/or devices. For example, the tissue image processing host computer system 202 can operate in a networked environment using logical connections to one or more network server computer systems (not shown). Communications may be via a wired and/or wireless network architecture, for instance wired and wireless enterprise-wide computer networks, intranets, extranets, and the Internet Other embodiments may include other types of communication networks including telecommunications networks, cellular networks, paging networks, and other mobile networks.

As explained herein, the tissue image processing host computer systems 202 may perform human tissue image correlation, image analysis, normalization and/or correction of optical exposure, spectral and spatial distribution in order to compensate for the surface reflections, sub surface tissue interactions and spatial orientation of the excitation and imaging axes to the subject tissue.

The tissue imaging and tissue image processing system 200 should be flexible such that clinicians can model tissue image data in different forms in order to cross reference and compare data from various spectral components and/or from different digital images. The ability for human interpretation between images is substantial and the tissue imaging and tissue image processing system 202 may enable variations to be seen between images, even when the spectral and spatial optical conditions or the image resolution or sensitivity are compromised or vary between times of image capture.

The use of the tissue image processing host computer system 202 to correct an image involves more than adjusting the same exposure levels and white balance. The introduction of a color card or fiducial marker into the field of view of the digital camera or image can enable the tissue image processing host computer systems 202 to automatically make corrections corresponding to the spectral effects in a tissue sample due to the complex interactions of light absorption, reflection and fluorescence and to automatically make spatial corrections to correct errors or differences due to the three dimensional characteristics and the orientation of the tissue imaging system 100 in Cartesian space.

The three dimensional shape, volume and depth of infiltration of a skin lesion are significant factors for ongoing clinical analysis. The tissue image processing host computer system 202 (FIG. 3) uses computer image processing methods on digital images or digital photographs to normalize much of the information, and to enhance critical features such as Lesion Shape and lesion borders and metabolically active areas that can aid in clinical analysis and diagnosis. The tissue image processing host computer 202 may produce appropriate digital or physical reports 270.

While the tissue imaging system 100 is described in terms of a digital camera and an excitation source 106 such as a light source or Xenon flash tube, other types of sensors such as spectrometers and other types of modulated excitation (e.g., light) sources could be employed. The tissue image processing host computer system 202 executes one or more computer software programs, processes or algorithms to perform various image processing techniques on the optical spectral data from the captured digital image. The host computer system is programmed to create a virtual three dimensional reconstruction or three dimensional digital model of the lesion, and to add multispectral data and image timeline data to the digital model or to a data structure associated with the digital model. The resulting digital model may be displayed as images on an appropriate device (e.g., LCD display, cathode ray tube display). Analysis of differences from normal versus lesion data in a static or timeline image sequence can be used by clinicians to evaluate the significance of any changes. The tissue image processing host computer system 202 may also be programmed to establish a baseline of what is normal for a given patient from an optical/molecular perspective, and this data used to contribute to the normalization of digital images or be used in a timeline as at least part of a diagnostic test.

Figure 4:
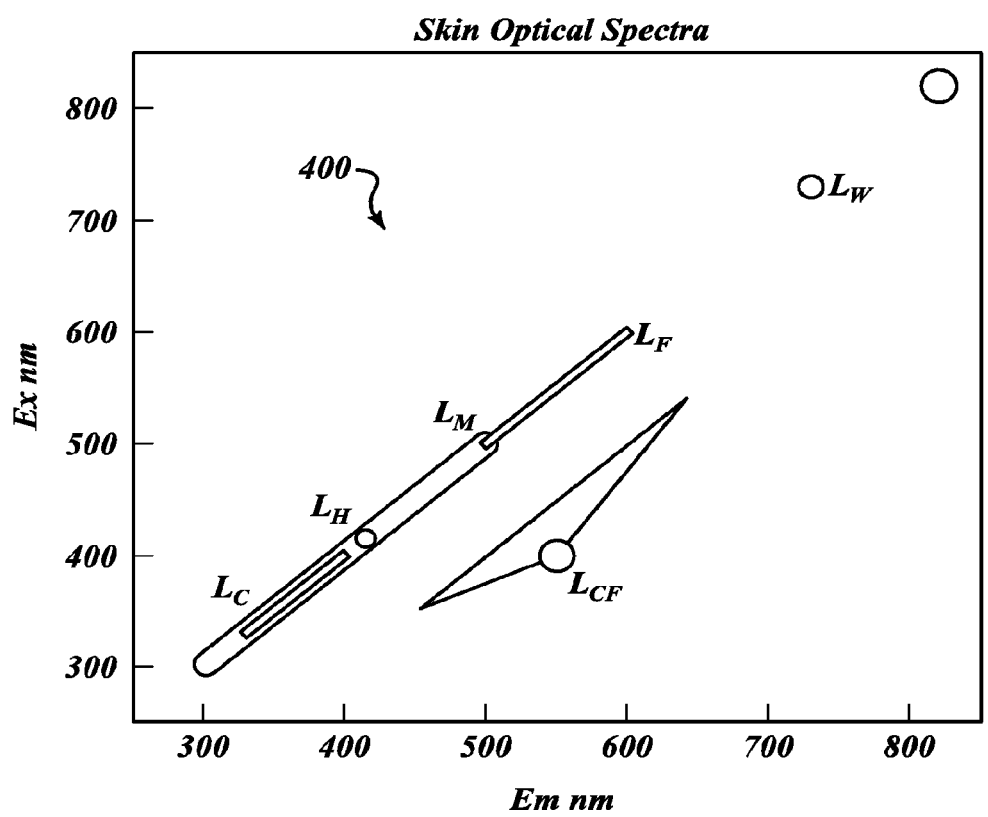
FIG. 4 is a graph that illustrates optical spectra of skin tissue with particular consideration for optical layers that make up a basis for comparative analysis, according to one illustrated embodiment.

FIG. 4 shows a graph 400 that illustrates optical spectra of skin tissue with particular consideration for optical layers that make up a basis for comparative analysis, according to one illustrated embodiment.

Characterizing the Optical Inhomogeneity

The tissue image processing host computer system 202 is programmed to correct for electromagnetic radiation returned from the tissue 102 (FIG. 1). For example, the tissue image processing host computer system 202 may correct the reflected light spectra, in the visible portion of the electromagnetic spectrum, of the skin area surrounding a skin lesion. Electromagnetic radiation (e.g., light in the visible and non-visible portions the electromagnetic spectrum) undergoes absorption and multiple scattering in the skin and is back scattered and re-emerges carrying information which characterizes or is indicative of certain physical characteristics of the structure of the skin and/or the lesion. The propagation and attenuation of electromagnetic radiation of certain wavelengths (e.g., light) varies for the different layers of the skin. The tissue imaging and digital image processing system 200 captures data regarding the spectral distribution of the electromagnetic radiation (e.g., light) which is reflected and/or back scattered and/or fluoresces from the tissue (e.g., skin, lesion). The tissue image processing host computer system 202 can separate the wavelengths or wavebands in the digital image, and compare the ratios of the respective radiant spectral intensity of the wavelengths or wavebands. This allows for evaluation of specific areas within a single image. This also allows for direct comparison at a later date to the data obtained from other images of the same tissue 102 (FIG. 1) or region of interest 118 (FIG. 2). In this way, a spectral distribution of certain areas of the digital image can be used to manage or aid in the interpretation of a digital image or timeline (i.e., sequence) of digital images. Further, the data from the digital image or sequence of digital images can be used to aid in the interpretation of the molecular structure of the subject tissue.

In use, the tissue imaging system 100 (FIG. 1) may capture a first subject digital image at a first time, and may capture further digital images at later times. Thus, the captured digital images may represent a sampling of the same scene or object or area at different times, and/or under different optical conditions. The tissue image processing host computer system 202 transforms the first subject digital image $I_1$ into a defined coordinate system and certain conditions are highlighted within an image layer $L_n$ or as metadata. One layer might represent the relationship between various optical spectra. As further or sequential digital images are added $I_{1+n}$, tissue image processing host computer system 202 can compare those digital images on a layer to layer $L_{1...n}$ basis by registering the new digital image in spatial coordinates and optical relationships. Deformation of the subject digital image due to either poor imaging technique, or morphological change is made to evaluate optical changes at specific coordinates in the digital image within the layers $L_n$ or compare the changes to the variations from the first subject digital image $I_1$ or other layers in different digital images along a timeline.

$$I_1 \rightarrow L_{1...n}$$

$$I_2 \rightarrow L_{1...n}$$

In this manner, the tissue image processing host computer system 202 compares the layers of each digital image such as the difference of one layer to the average:

$$(I_1L_1 + I_2L_2)/2 - I_1L_1$$

In which case the tissue image processing host computer system 202 may recalculate the individual pixel values. In certain cases only the pixel values of specific x, y coordinates would be used.

One layer might represent the relationship between various optical spectra. Optical changes such as spectral changes or optical density at specific coordinates in the digital image $O_{(xn, yn)}$ can be referenced to compare the changes to the variations from another subject digital image $I_{1+n}$, such as the coordinates that were indicative of the lesion area. Alternatively, or additionally, a numerical value could be created by a clinician identifying a cross sectional area where a histogram (hist) would be generated to visualize the probability density of certain optical spectra within, or between, layers such as for the set of specific x, y values in chosen layers:

$$\text{hist}\{I_1L_1(x_n, y_n)\}$$

Histograms or other types of analysis such as derivatives or ratios can be used to determine the changes between areas of interest 118 (FIG. 1) within a layer or between layers.

Fiducial Marker

One or more fiducial markers 116 (FIG. 1) may be employed to provide information in the digital images which allows the tissue image processing host computer system 202 to perform various image processing acts (e.g., normalization, comparison, three dimensional modeling). As explained in detail below, the fiducial markers 116 may take the form of physical objects (e.g., physical media) which are placed at, on, or proximate the region of interest 118 (FIG. 1) of the tissue 102 for image capture Alternatively, or additionally, the fiducial markers 116 may be virtual, taking the form of structure light projected to illuminate an area at, on, or proximate the region of interest 118 (FIG. 1) of the tissue 102 for image capture. Whether physical fiducial markers, virtual fiducial markers or both are employed, a knowledge of baseline or starting physical characteristics of the fiducial markers 116 is used to identify differences (e.g., spectral, geometric or topological) between the baseline or starting physical characteristics and how the fiducial markers 116 appear in a captured digital image. Such allows characterization of differences between captured images, which differences may arise due to system variations or ambient environment variations, which variations are unrelated to variations in the tissue itself.

Figure 6:
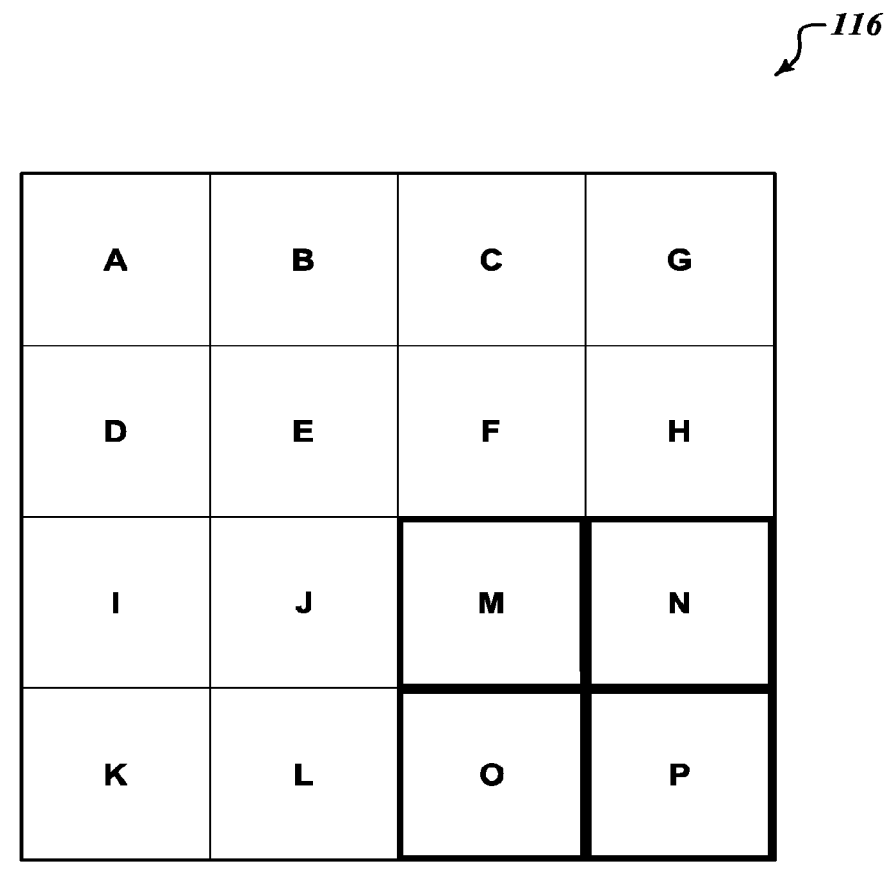

As best illustrated in FIG. 6, the fiducial markers 116 have a defined shape or two dimensional profile. While illustrated as rectangular, other shapes may be employed, for example hexagonal, octagonal, or another polygon. In some instances, fiducial markers may have other non-polygonal profiles, for example oval or circular, although such may be less preferable since such non-polygonal shapes may limit the amount of information regarding orientation which can otherwise be discerned from the appearance of the fiducial marker 116 in a digital image. In such instances it may be advantageous to include additional defined shapes in the fiducial markers 116, for radial line segments.

Also as best illustrated in FIG. 6, the fiducial markers 116 may take the form of a plurality of discrete portions, denominated as sections herein. Each portion or section may have a respective characterizing physical property, for example a respective spectral electromagnetic radiation absorption or reflectance property or characteristic. Thus, for example, the fiducial marker 116 may appear as an array of different color, grey scale or white sections, each section preferentially absorbing certain wavelengths or bands of wavelengths while reflecting, back scattering or fluorescing other wavelengths or bands of wavelengths. While the sections may typically arranged in a two dimensional array, such as illustrated in FIG. 6, some fiducial markers may take the form of a one dimensional or linear array, while other fiducial markers may include an unordered array or collection of sections. The characterizing physical properties (e.g., spectral absorption and/or reflectance properties) and relative positions of each sections are known to the tissue image processing host computer system 202, at least during image processing, as is the baseline or starting shape or profile.

These sections may be organized by function or characterizing property. For example, a number of sections may form a color chart, including primary/secondary color portion (sections labeled A-F), skin pigment reference colors portion (sections labeled G-H), black, white, grey scale portion (sections labeled I-L). A number of sections may form a tissue phantom portion (sections labeled M-P). Each portion may respectively include one or more distinct sections with respective physical characteristics such as selective wavelength absorption, reflectance and/or florescence.

For example, the primary/secondary color portion (sections labeled A-F) of the color chart may take the form of a physical arrangement of defined primary and/or secondary colors, which can be used for color registration within the image space. For instance, sections A-F may appear as blue, teal, green, magenta, red, and yellow, respectively. The grey scale portion of the color chart may be an arrangement of sections used as a middle gray reference of in the order of 13-18% reflectance, and the black or white balance portion of the color chart may be in the order of 90% reflectance and used by the tissue image processing host computer system 202 to compensate for variations in apparent optical excitation such as variations in excitation source to subject distance (i.e., distance between excitation source 106 and target tissue 102). For instance, sections I-L may appear as dark grey, white, black, light grey, respectively. For instance, the sections G and H may be brown and a Caucasian skin tone (e.g., tan), respectively. For instance, the sections M-P may appear as violet, blue, purple and light blue, respectively.

Corrections are to be used for calibration of the light returned (e.g., reflected, back scattered, fluoresced) from the subject tissue 102. The tissue image processing host computer system 202 can correct multiple digital images by comparing and adjusting for the appearance of the primary/secondary color portion (sections labeled A-F), black, white balance and grey scale portion (sections labeled I-L) in the digital image based on the known values of the various sections. In more complex optical correlation between digital images, tissue phantom portion (sections labeled M-P) on the fiducial marker 116 may be used for correlation of light from deeper tissue and to minimize the effect from surface reflection. Thus, the tissue image processing host computer system 202 uses the appearance of the fiducial marker 116 in digital images to measure and correct for variations in spectral power distribution from one digital image to another digital image.

Figure 5:
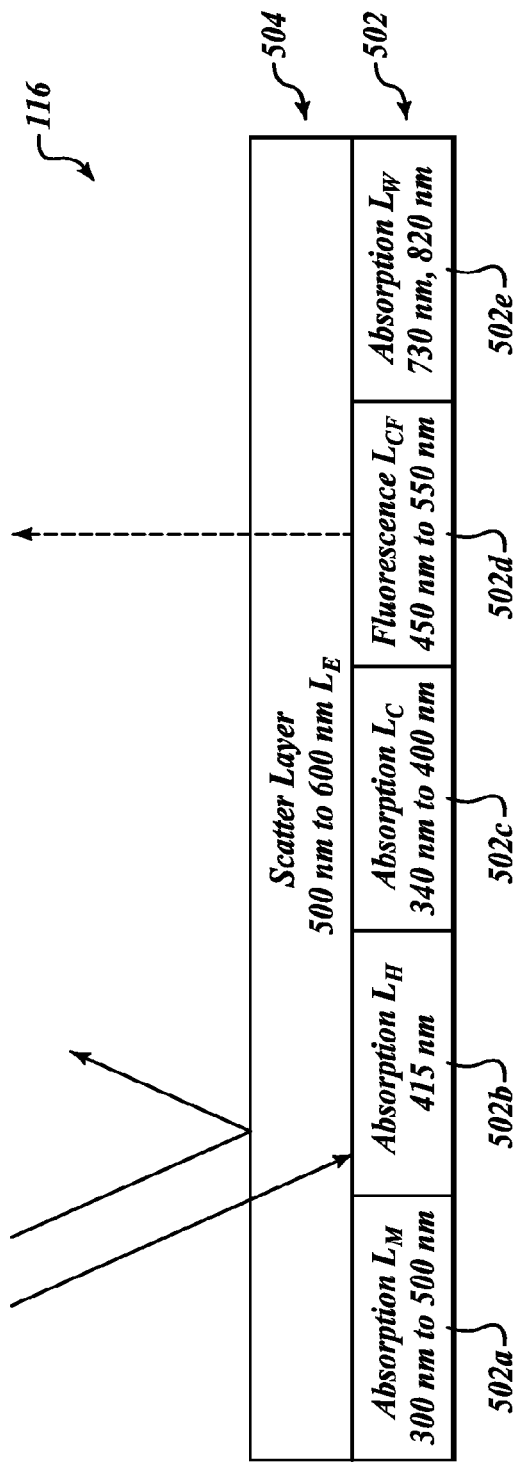
FIG. 5 is a cross sectional view of a fiducial marker optical phantom with a reflective layer overlying a number of reference sections of the tissue optical layers, according to one illustrated embodiment.

As best illustrated in FIG. 5, a tissue phantom fiducial marker 116 is a structure to correct for the reflection and the backscatter of the dominant wavebands of the skin. The tissue phantom portion of the fiducial marker 116 includes a wavelength selective portion 502 that has an overlying surface or coating 504. The overlying surface or coating 504 causes some surface scatter while also allowing transmission of some light, and has a known optical density $O_n$. The wavelength selective portion 502 of the tissue phantom portion may include a plurality of sections or swatches of different colors (five illustrated in FIG. 5) 502a-502e that advantageously represent the spectral absorption and reflection of collagen and also of hemoglobin. The overlying surface or coating 504 may advantageously take the form of a matt surface that yields a five to seven percent reflection.

Figure 7:
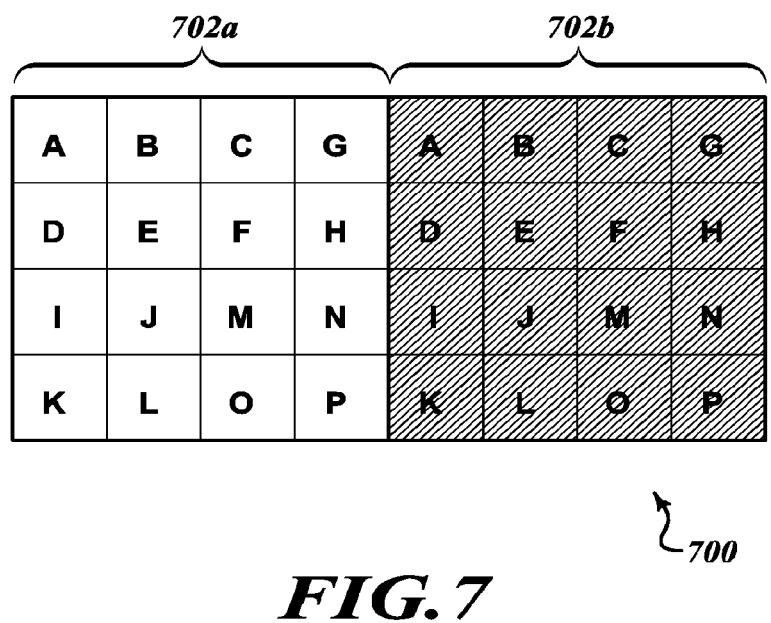
FIG. 7 is a top plan view of a fiducial marker including a first portion having a first color chart and a scattering layer overlying the first color chart, and a second portion having a second color chart which is not overlaid by a scattering layer.

FIG. 7 shows a physical fiducial marker 700, according to one illustrated embodiment.

The physical fiducial marker 700 has a first portion 702a which includes a scatter layer 702a overlying a first plurality of sections A-P. The sections A-P of the first plurality each have respective different colors or wavelength selective spectral absorption, reflectance, and/or florescence characteristics (sixteen illustrated, labeled A-P), identical or similar to those discussed above. The physical fiducial marker 700 has at least a second portion 702b which omits the scatter layer overlying a second plurality of sections. The sections A-P of the second plurality each have respective different colors or wavelength selective spectral absorption, reflectance, and/or florescence characteristics (sixteen illustrated, labeled A-P), identical or similar to those discussed above.

Each portion 702a, 702b may include the same set and spatial arrangement of sections or colors. For example, each sector A-P of the first portion 702a may be a respective one of 16 colors, while each sector A-P of the second portion 702b may be a respective one of the same 16 colors. The colors of the sectors A-P of the second portion 702b may be spatially arranged in the same order or relative positions with respect to one another as the order or relative positions of the sectors A-P of the first portion 702a. Thus, sector A of both the first portion 702a and the second portions 702b may both be, for example red or otherwise have the same wavelength selective spectral absorption, reflectance and/or florescence characteristics.

The inclusion of a scatter layer 504 (FIG. 5) on the first portion 702a and omission of such from the second portion 702b facilitates automated normalization that corrects for spectral distribution of a sensor (e.g., image sensor such as an array of charge coupled device, or CMOS image sensor). Notably, sensors may respond differently in changing ambient conditions, such as changing light and/or temperature conditions. The correction for sensitivity across the spectral distribution and scatter at specific wavebands can be used to optimize the image processing, especially to compare the ratios of sectors.

The fiducial marker 116 (FIGS. 1 and 2) may be virtual, being formed by projecting structured light from the excitation source 106 (FIG. 1) which forms a pattern of light on the subject tissue 102. The projection may be of multi-dimensions and include variations of optical spectra. The projection may be sweeping by use of a laser scanner, holographic scanner or monochromator or may achieved via one or more filters or diffractive optical lenses to fit over the excitation source 106 (FIG. 1) for example a flash tube or bulb of a digital camera 104. Using structured light allows the tissue image processing host computer system 202 to perform automated tissue layer analysis due to the variations in triangulation with multiple spectra. Variations in optical spectra can be used to measure or otherwise determine the molecular optical character of the subject without interference from out of band wavelengths. The sensor or digital camera 104 captures the incident light from the surface of the subject tissue 102, which provides a digital image containing information which can be analyzed and/or processed to create an image map.

Figure 8:
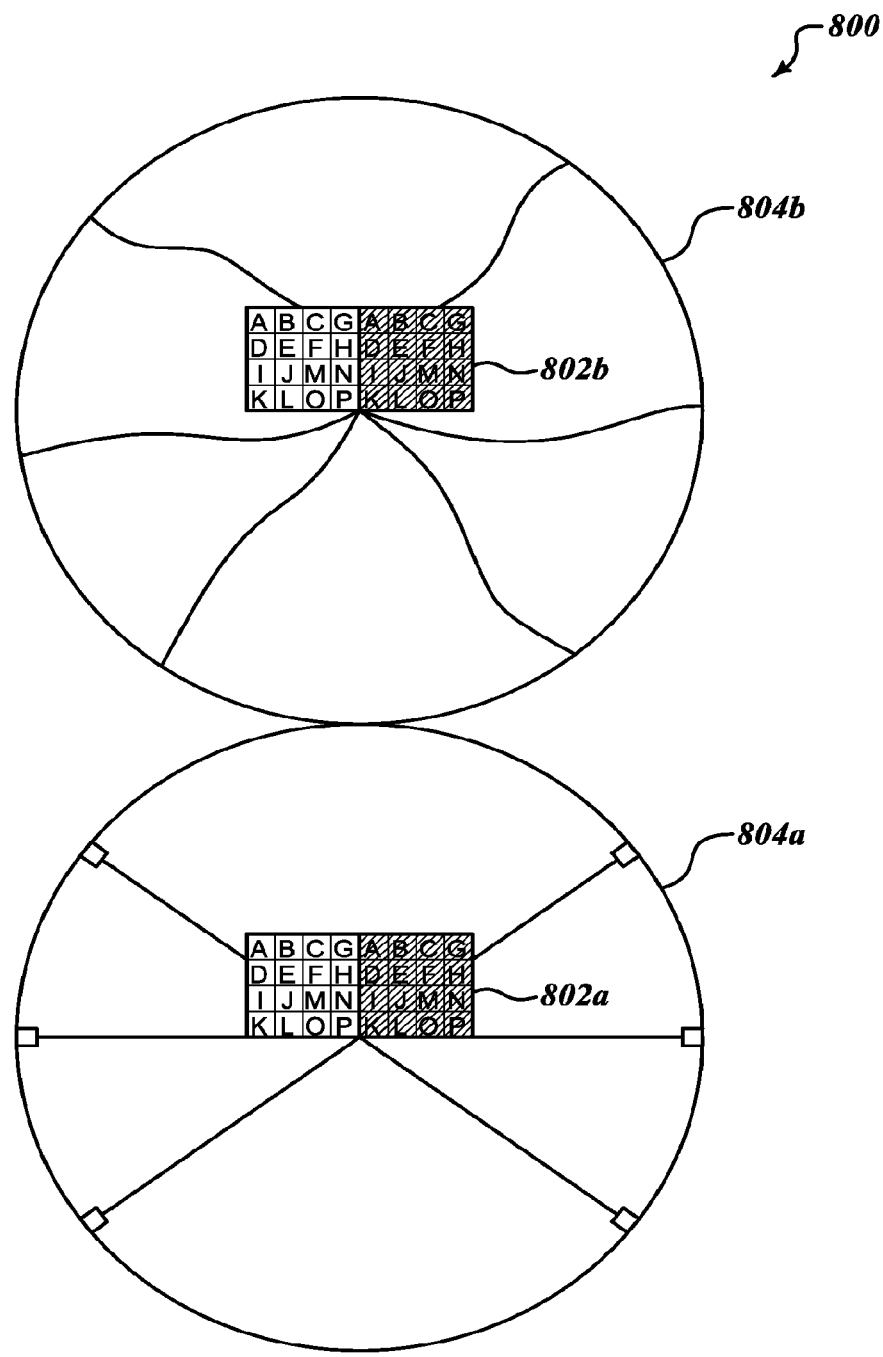
FIG. 8 is a top plan view of a physical and a virtual fiducial marker on at flat surface and one a surface that is not flat, according to one illustrated embodiment, illustrating the change in geometry which is perceptible via variation in geometric elements or shapes of the fiducial marker.

FIG. 8 shows a physical fiducial marker 802a, 802b (collectively 802) and projected or virtual fiducial marker 804a 804b (collectively 804) used in combination.

The physical fiducial marker 802a, 802b has a defined shape or profile, rectangular in FIG. 8, and includes a plurality of sectors, each with respective spectral absorption, reflectance or florescence characteristics, as discussed above. When projected onto a flat surface, the projected or virtual fiducial marker 804a has a defined shape. For example when projected onto a flat surface, as illustrated in the lower portion of FIG. 8, the projected or virtual fiducial marker 804a may have a circular profile and a plurality of straight radial line segments which emanate from a center point of the circular profile. However, when projected onto a surface that is not flat (e.g., lesion), the projected or virtual fiducial marker 804b has a shape that conforms to the non-flat surface. For example when projected onto a lesion, as illustrated in the upper portion of FIG. 8, the projected or virtual fiducial marker 804b the profile may be changed and/or the radial line segments may no longer be straight but rather reflect the three dimensional contours of the lesion.

Thus, the physical fiducial marker 802 and projected or virtual fiducial marker 804 can be used in combination to assure that the benefits of each are utilized. The physical fiducial marker 802 may advantageously provide improved normalization and correction for spectral character, while the projected or virtual fiducial marker 804 may advantageously provide improved shape correlation to spectral abnormalities.

The projected fiducial marker 804 can be of a form that provides information which allows the tissue image processing host computer system 202 to effectively analyze three dimensional tissue (i.e., tissue that has a relatively large change in curvature or change along the Z-axis over the XY area of tissue being imaged), such as the cervix. A scatter distribution can be obtained in combination with shape measurement. The tissue image processing host computer system 202 can compare this information at various wavelengths to create a spatial and spectral map of the tissue and the optical characteristics of the tissue.

As noted above, the projected or virtual fiducial marker 804 can be used as various shapes to enable the collection of both spectral and spatial information. The projected or virtual fiducial marker can use optically discrete parameters, for example projected lines, so as to measure the distortion of the area of interest. The reflective nature of the subject tissue can be measured or otherwise determined or assessed as local distortion of the projected line such as optical saturation of the sensor versus incident reflection. In this respect it is noted that two spatially identical optical line projections at different wavelengths display different scatter characteristics. The tissue image processing host computer system 202 can measure or otherwise determine such for various wavelengths of light to get a better measure of the reflection, absorption, transmission and fluorescence at coordinates within the digital image. For example, two spatially identical projections of a line, varied only in their wavelength, might have greater reflectance at one point at a specific wavelength versus another. This enables the post processing of digital images to account for reflectance artifacts.

Figure 9:
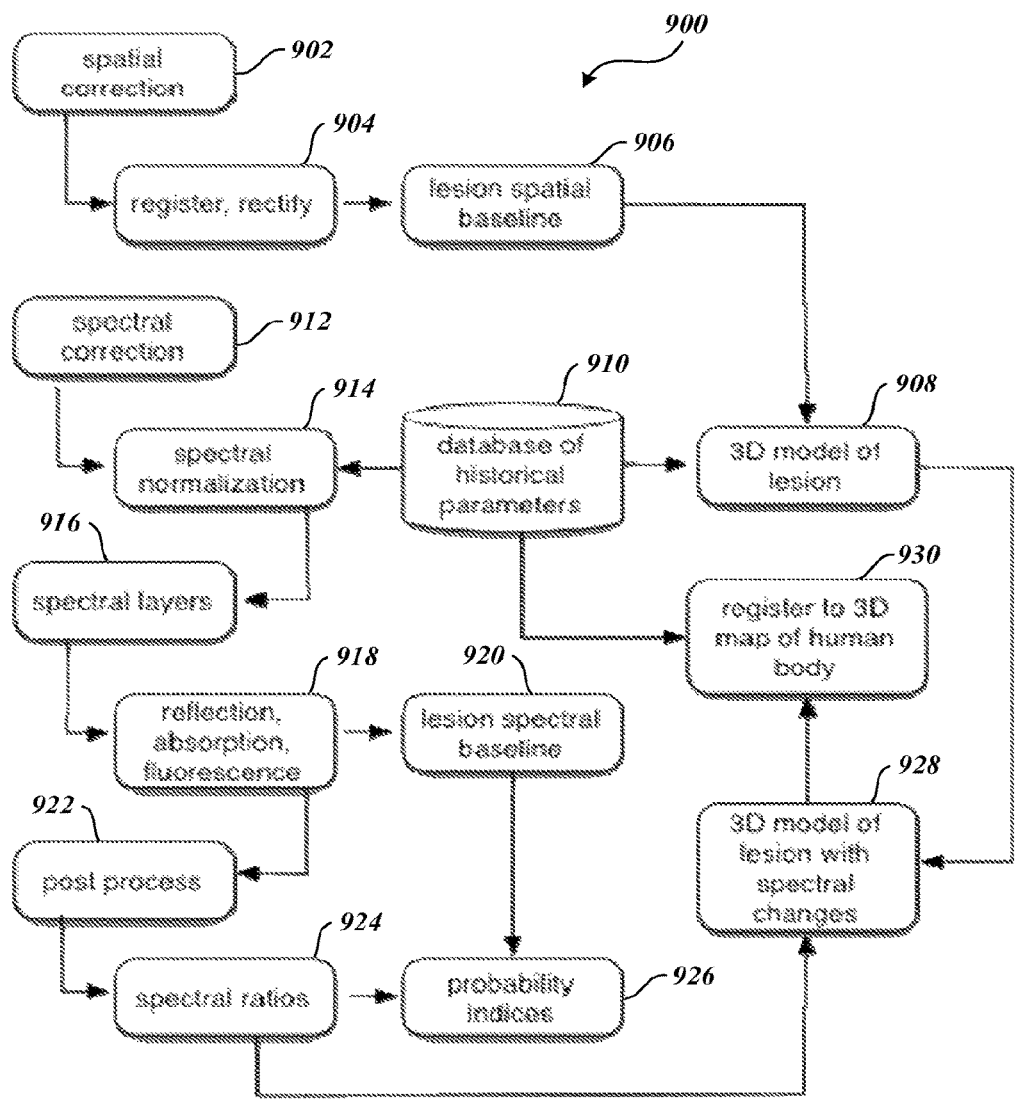
FIG. 9 is a flow diagram illustrating an operation of a tissue imaging and digital image processing system, according to one illustrated embodiment.

FIG. 9 is a flow diagram illustrating a method 900 of operating a tissue imaging and digital image processing system 202, according to one illustrated embodiment. The method 900 is exemplary. In use, the method 900 may include additional acts, omit some acts, and/or perform acts in different orders. The method 900 is presented as an overview. Many of the specifics of performing the various acts of the method 900 are described in detail herein.

At 902, the tissue image processing host computer system 202 performs spatial correction on a digital image. The tissue image processing host computer system 202 may rely on the difference between how the fiducial marker appears in the digital image and a known appearance of the fiducial marker. Spatial correction may, for example correct for various digital imaging system misalignments and is generally discussed elsewhere herein.

At 904, the tissue image processing host computer system 202 registers and/or rectifies the digital image. Image registration and/or rectification are discussed in more detail elsewhere herein.

At 906, the tissue image processing host computer system 202 may generate a region of interest spatial baseline (e.g., lesion spatial baseline). The spatial baseline may facilitate comparisons over time. Spatial baseline generation is discussed in more detail elsewhere herein.

At 908, the tissue image processing host computer system 202 may generate a three dimensional model of the region of interest (e.g., lesion). The tissue image processing host computer system 202 may employ information stored in a database of historical parameters 910, stored on one or more nontransitory computer readable storage mediums. The three dimensional model facilitates comparisons, and is discussed in more detail elsewhere herein.

At 912, the tissue image processing host computer system 202 may perform spectral correction on the digital image. The tissue image processing host computer system 202 may rely on the difference between how the fiducial marker appears in the digital image and a known appearance of the fiducial marker. Spectral correction may, for example, correct for various differences in imaging conditions, for example variations in lighting, and is generally discussed elsewhere herein.

At 914, the tissue image processing host computer system 202 may perform spectral normalization on the digital image. The tissue image processing host computer system 202 may employ information stored in the database of historical parameters 910 to perform spectral normalization. Spectral normalization is discussed in detail elsewhere herein.

At 916, the tissue image processing host computer system 202 may create spectral layers in the digital image file, storing spectral information thereto Layers of the digital image file are discussed in detail elsewhere herein.

At 918, the tissue image processing host computer system 202 determines reflection, absorption, fluorescence values or characteristics for the digital image. As described elsewhere herein, the tissue represented in the image may be characterized by is spectral characteristics, in particular in the particular wavelengths of wave bands which the tissue, or portions thereof, absorb, reflect or fluoresce. Determination of the reflection, absorption, fluorescence values or characteristics are described in detail elsewhere herein.

At 920, the tissue image processing host computer system 202 generates a region of interest spectral baseline (e.g., lesion spectral baseline). The spectral baseline allows spectral changes in the region of interest to be easily and accurately compared and identified. Generation of spectral baselines are discussed in detail elsewhere herein.

At 922, the tissue image processing host computer system 202 performs post processing. There are numerous possible post processing procedures, which are described elsewhere herein.

At 924, the tissue image processing host computer system 202 determines spectral ratios. As described herein, spectral ratios may be particularly advantageous for allow comparisons within a digital image or between digital images. The determination and use of spectral ratios are described in detail elsewhere herein.

At 926, the tissue image processing host computer system 202 determines probability indices. The tissue image processing host computer system 202 may employ the lesion spectral baseline generated at 920 in determining the probability indices. Probability indices facilitate the diagnosis of tissue, such as lesions, and the generation and use of such are discussed in detail elsewhere herein.

At 928, the tissue image processing host computer system 202 generates a three dimensional digital model of the region of interest (e.g., lesion) incorporating the spectral changes. The generation of the three dimensional digital model and the benefits thereof are discussed in detail elsewhere herein.

At 930, the tissue image processing host computer system 202 may register the three dimensional digital model generated at 928 with a three dimensional map of a human body or portion thereof. The tissue image processing host computer system 202 may employ information from the database of historical parameters generated at 910. The registration may facilitate analysis and/or diagnosis, as discussed in more detail elsewhere herein.

Normalization

In some embodiments, the tissue image processing host computer system 202 may normalize an image time series (i.e., temporal sequence of digital images). Those digital images may have been captured over a relatively long time (e.g., decades, years, months) at any variety of frequencies or intervals, and/or over a relatively short time (e.g., weeks, days, hours) at any variety of frequencies or intervals. In the case of multiple digital images taken over variable ambient conditions, any difference of the spectral distribution between the reflective character of a digital image, such as those taken in low ambient light versus digital images created with electronic flash, will reduce the probability of confidence in an image correlation. Such a case will require numerical methods to correct or normalize the digital images.

The monotonicity of certain spectral relationships may be outside or approaching the limit of the normal spectral distribution. This might be typical for the case where a digital image is normalized to the fiducial marker 116, yet still requires to be normalized based on the spectral markers such as hemoglobin and collagen.

The presence by measure of reflective, absorptive, transmissive or fluorescent light, or relationship of one spectra to another is computationally bounded within certain limits of what is normal. Normal may be determined by the spectral distribution ratios of healthy tissue in the person of interest or in comparison to a population. Once there has been a normalization, certain optical relationships can be analyzed such as a probability distribution. One example of this is the optical density compared to the percentage of the optical spectra that can be attributed to that of collagen. Another example is to remove the spectra that are attributed to the surface skin and allow for sub surface analysis.

In the case where spectral distribution is corrected by numerical methods, a computed distribution that results in increases of a waveband that might normally cause fluorescence will not be able to assign fluorescent values outside of what is considered normal. However, by analysis the distribution can be automatically assessed by the tissue image processing host computer system 202 to determine if there are corresponding increases in spectra that would relate to absorption and fluorescence. To correct for fluorescence in a time series of numerically processed digital images requires then that the digital images are assessed or analyzed within a probability index.

Some embodiments may advantageously employ digital images that are displayed in layers assigned to the wavebands of excitation and with a probability index that allows certain images to be weighted in their diagnostic value.

The monotonicity of spectral changes, whether individual spectra or comparative changes between spectra may show a trend; for instance, a trend that highlights a decreasing amount of collagen in one tissue versus another tissue. The tissue image processing host computer system 202 may consider or assess a linearity of the function versus the normalization.

Exposure and Color Correction

Exposure may vary with both the angle of incidence, the relative angle of the illumination (e.g. flash) to the subject tissue 102 (FIG. 1), the irradiance of the illumination and the spectral distribution of the illumination, the orientation of the subject tissue 102 from one digital image to another digital image with respect to the optical axes, the distance and angle of the imaging optics to the subject tissue 102, any filters 108, 112 in the optical paths (arrows in FIG. 1) and shutter speed, aperture and sensitivity of the imager or image capture device 104.

In at least some embodiments, the tissue image processing host computer system 202 is designed to compensate for the optical effects that vary with the optical exposure. Exposure may be initially established by comparing the features of the fiducial markers 116 and correction for spectral distribution of the excitation source 106 (FIG. 1) and then the tissue characteristics. Compensation for reflection involves separation of the surface effects from the subsurface effects.

In at least some embodiments, color correction includes exposure analysis based on the fiducial markers 116, modeling of the tissue depth profile, and further includes use of information of the ratios of lesion colors, width, fluorescence and reflection to that of surrounding tissue in a two dimensional normalization.

In at least some embodiments, color correction includes exposure analysis based on the fiducial markers 116, modeling of the tissue depth profile with greater degrees of specificity including spectral correction of non-lesion tissue components such as optical biomarkers from subsurface tissue excitation including, blood, oxygen, glucose, collagen, flavins, elastin, tryptophan, NADH etc.

Notably, the apparent optical exposure may also vary due to changes in the subject, including hydration, blood flow, temperature and the ratios of the natural skin components including epidermis, melanin, hemoglobin, collagen, bilirubin and other chromophores such as carotenoids and porphyrins. Further the apparent optical exposure may be altered by the use of topical creams, cosmetics or by drug and food interactions with the natural skin components. In such situations, the tissue image processing host computer system 202 then adjust the digital image to a baseline normal of the reflected light, and remove any artifacts, and the ratio of subsurface backscatter from one digital image to another digital image can then be more easily compared by using a subsurface ratio.

In at least some embodiments, the tissue image processing host computer system 202 uses the ratios of the optical scattering of hemoglobin to that of collagen as a reference to adjust and normalize the optical exposure of the subsurface.

Optical Ratios

The reflective properties of the epidermis of one person versus another person can vary significantly as so can the ratios of hemoglobin, collagen, melanin to epidermis from person to person. As a result, the complexity of human skin requires that in order to accurately reference one digital image to another digital image, that an accurate model is representative of each person. A system of optical layers for each image $I_1L_1$ that conforms to the principle optical absorption bands is used to separate the optical spectra as further described below.

An Epidermal Layer where scattering dominates absorption in the visible spectrum of 500 nm to 600 nm $I_1L_E$.

A Melanin Layer where the melanin absorption in the spectrum of 300 nm to 500 nm $I_1L_M$ may be characterized by the optical density O or computed by comparison to other spectra from various molecular optical sources at different wavelength $O\lambda$. Melanin does not have a defined peak in the visible but its absorption coefficient decreases with the longer wavelengths.

A Hemoglobin Layer where the hemoglobin absorption in the visible spectrum primary absorption of oxyhemoglobin peaks at 415 nm $I_1L_H$. Adjustments to the hemoglobin layer may be made by comparison to deoxyhemoglobin such as primary absorption peaks at 430 nm or by using the absorption of hemoglobin to correct for artifacts in other layers, such as secondary absorption peaks for oxyhemoglobin at 542 nm and 577 nm, and secondary absorption peaks for deoxyhemoglobin at 555 nm.

A Collagen Layer where the collagen absorption is measured in the visible portion of the electromagnetic spectrum in the near UV such as the optical region between 340 nm to 400 nm $I_1L_C$. In addition, a fluorescence peak would be measured in comparison to the absorption in the optical wavelengths between 450 nm to 550 nm $I_1L_{CF}$.

A Water Layer where the water absorption is measured in the visible and NIR spectrum at peaks 730 nm, 820 nm $I_1L_W$.

In at least some embodiments, the tissue image processing host computer system 202 uses the ratios of the optical scattering of the epidermis to that of melanin as a reference to adjust and normalize the exposure of the subsurface.

The tissue image processing host computer system 202 can use a normalized ratio of one known spectral property to another to create a personal optical profile. These spectral ratios or other ratios can be used as a personal optical profile for each person.

Morphology Correction

Correction for correlation of digital images should also include color correction information in order to establish the border parameters. The tissue borders are often areas where lesions can be analyzed for changes in tissue that might include fluorescence and reflection changes. Hence the control of light exposure will have an impact on the measurement of borders and boundaries which are used in physical size and growth comparisons.

The analysis of boarders then can be made by measuring or otherwise determining the subsurface components of the optical spectral components of the tissue. The amount of collagen in tissue decreases as tissue becomes neoplastic. Other components such as NADH increases and changes in blood flow are known to be synonymous with lesions and serve as excellent markers for lesion boarders.

Lesion boarders can also be established by comparison of the surface optical spectra to the subsurface spectra. This further allows for a reference to be used in a timeline. A numerical index based on the optical characteristics can be established.

In a multiple image series, normalizing the surface reflection in each digital image would be achieved by normalizing the color markers. Such allows accurate comparison of the Epidermal Layer in the visible spectrum of 500 nm to 600 nm $I_1L_E$ to the Melanin Layer in the spectrum of 300 nm to 500 nm $I_1L_M$ and comparing and adjusting ratios as required at proximity to lesion site. Subsurface scatter may be advantageously normalized via measurement or determination of ratios such as those of hemoglobin/collagen, a relative Hemoglobin Layer where absorption of oxyhemoglobin peaks at 415 nm $I_1L_H$ to the Collagen Layer where absorption is between 340 nm to 400 nm $I_1L_C$ or a fluorescence peak in the optical wavelengths between 450 nm to 550 nm $I_1L_{CF}$ and comparison and adjustment of ratios as required at proximity to lesion site border.

Once the borders spectral distribution has been established, the borders' spectra can be compared to the surrounding tissue and a lesion map can be generated by visual analysis or by automated image processing methods or techniques that track the pixel characteristics in the digital image. The lesion map may be multidimensional and have reference layers such as surface, sub-surface and other layers or depth characteristics as may be determined from the spectral analysis, such as areas of molecular activity, blood flow or tissue density.

In some cases tissue image processing host computer system 202 may combine the optical data with spatial data to create true three dimensional digital models of the lesions or combined with physical anatomical models, for instance in a form of rubber sheeting to create pseudo three dimensional physical models.

Growth comparisons are the combination of changes in color and changes in shape. The color data is either the absolute changes in total color or the variation in the layers. Either or both can be used to monitor change at any x, y coordinates, or as a method to reference the changes in a sample such as a cross section and its normalized spectral distribution.

Combined Methods of Rectification.

The shape of the fiducial marker 116 (FIGS. 1 and 2) allows for image rectification, but the lesion or some area or region of interest 118 in the tissue 102 must be used to relate images to each other. In some cases, this can be done manually with obvious image characteristics. In other cases, it can be done automatically (i.e., computationally by a processor such as a digital microprocessor) by examining areas within the image layers that have a notable and repeatable spatial and spectral variation such as the difference between image layer coordinates in a time series:

$$I_{2\ldots n}L_C(x_n,y_n)/I_1L_C(x_n,y_n)$$

Relative spherical and chromatic aberrations can be caused by the optical system in normal function, or by variance to the conditions or settings used such as excitation irradiance, focal length and aperture.

In at least some embodiments, the tissue image processing host computer system 202 performs digital image rectification which converts digital images to a standard coordinate system for registration and a standardized method of optical correlation. This is done by matching areas of the tissue 102 (FIGS. 1 and 2) or the fiducial marker 116 in the source image $I_1(x_n,y_n)$ with areas of the tissue 102 or the fiducial marker 116 within the time series images $I_{1\ldots n}(x_n, y_n)$. This process is designed to overcome difficulties in clinical imaging where accuracy or aberrations in area analysis cannot be well defined, or where the digital images or layers lack clearly identifiable points with which to correlate between the digital images. A time sequence of digital images can also be used to correct for distortion such as variations of optical aberrations in the tissue imaging system 100.

The shape of the tissue 102 may be rectified with a 3D topographic map of the body or simulation thereof to compensate for distortion from the tissue topography at the area or region of interest 118. The geometric correction of digital images requires calculating the distortion at each pixel or area, and then comparing the digital image to the proper location in the 3D topographical map. The digital image is registered when each pixel or area is placed in the correct precise 3D position or location. The adjustment may also take into consideration the excitation source 106 (FIG. 1) and sensor 104 orientations and locations. This method combines 3D model probabilities with measurements from digital images to provide precise, orthographically correct coordinate locations. This process registers digital images and areas or regions of interest 118 from digital images with x, y, and z coordinates. The displacement is then calculated for each area in the digital image, with variable resolution, and distortion is removed or measured or otherwise quantified. Multiple digital images can be analyzed, corrected, and mosaicked all at once by a bundle adjustment, in which interrelated sets of equations are used to find a globally optimal set of corrections across all of a number of digital images. Spectral conditions are handled in an analogous way by correlating light intensities for different color bands and then compensating for 3D influences of the digital model.

Diagnostic Protocol

One objective of providing normalized digital images is to enable clinicians to be able to make diagnostic decisions. Using the ABCD rules as would be considered normal in dermatology, the tissue imaging and digital image processing system 200 can provide data that would enable clinicians to interpret the data in a manner that provides a rapid and consistent method of diagnostic reference. Image morphology data would be available to automatically update the ABCD protocol with data about asymmetry, irregularity diameter and supplemental data regarding the evolving nature and form of and skin lesion.

In implementations, a vasodilator may be applied to the tissue 102 (e.g., skin) or taken orally to enable the measurement of changes in blood flow in the tissue, and to assist in contrast enhancement of the area or region of interest 118.

High Specificity Analysis

Optical analysis can be used to access the molecular components of tissue and can be used to characterize the physical changes in tissues. The tissue imaging and digital image processing system 200 may employ an optical tissue imaging system 100 (FIG. 1), which may include a digital camera 104. Such an optical tissue imaging system 100 may employ monochromatic light control structures, for example a grating or band pass filter, or a series of optical filters. Additionally, or alternatively, the optical tissue imaging system 100 (FIG. 1) may be operated in a controlled environment, where additional metadata or other information is stored in non-transitory storage media characterizing the ambient conditions. For example, metadata may characterize the orientation of the subject tissue to the optical axes, the use or presence of filters on both the irradiant source excitation and subject radiant emission imaging axes. In the case where "off the shelf" digital cameras 104 are used, the digital cameras 104 often have integral filters positioned over the sensor(s) to normalize the response of the sensor in the visible portion of the electromagnetic spectrum. In some cases, the visible portion of the electromagnetic spectrum is not desirable or the use of light in non-visible portions (e.g., UV or NIR) of the electromagnetic spectrum may advantageously enhance analysis. In this case, the filters could be removed or omitted to allow the maximum multi-spectral response of the wavelengths of interest.

In these manners, close control over the optical characteristics of the tissue imaging system 100 (FIG. 1) can be maintained and adjusted, and the tissue image processing host computer system 202 can be used for higher degrees of specificity than might otherwise be the case. Optimizing the variable conditions may assist in using the tissue image processing host computer system 202 for situations typical to clinical general practice. This could also become typical of a dedicated tissue imaging and digital image processing system 200 as might be used for colposcopy, dentistry, during surgery, or for other applications that require a high degree of precision.

Communications

In practical applications, the tissue imaging system 100 (FIGS. 1 and 2) and the tissue image processing host computer 202 (FIG. 3) may be remotely located from one another, for example at different sites or facilities. Communications of digital images can be made by comparing a series of films and not digital data. This would require the handling of the physical media, but ideally the communication of images is shared over a network, for example including the Internet. Digital images can be transferred from a camera 104 of the tissue imaging system 100 to a tissue image processing host computer 202 via the Internet and/or some other network(s). For example, digital images could be attached to an electronic mail message (i.e., email), or communicatively transferred in an encrypted format, for example via a Web based server. Various methods of data encryption or decryption may be used to ensure privacy as would be expected in the handling of medical data. Other methods could include physically delivering a disk or memory card to an image analysis service. In some cases the tissue image processing host computer 202 and the tissue imaging system 100 are in the same location and the tissue image processing host computer 202 would then create a laboratory imaging report 270.

Signal Enhancement

In a controlled environment, various techniques of signal enhancement can be used such as pulsed excitation sources 106 (FIG. 1) and digital filters (not shown) that allow for frequency or amplitude modulation or time filtering. For instance, detection of short time domain fluorescence would require sharp cut off of the excitation source 106. Correlation of triggering of optical excitation source 106 with sensor electronics allows for the use with frequency or amplitude methods, including electronic methods such as FM and BPSK or mechanical shutters and choppers. Detection of low light signals might be further enhanced by measuring and filtering the ambient signal noise.

Probability Index

In at least some embodiments, the tissue image processing host computer system 202 uses a probability index, which is the combination of distributed properties resulting from combined probability analysis of one or more variables including normalization, exposure correction, geometric correlation, color correction, signal to noise characterization and diagnostic protocols as would be used in a time series.

This can be applied using multivariate time series analysis techniques such as linear methods based on correlation functions or spectral decompositions or nonlinear approaches such as recurrence features and include the determination of heterogeneous data in subsurface layers, layer matching and morphological image matching.

Physical means of image correction can also be used to acquire optical metadata prior to the image acquisition. Optical filters can be used, such as spectral bandpass filters, polarizer's, or the addition of spectral indices that were created by using a spectrophotometer can be used to act as digital filters.

Operation is described below with respect to specific examples. It will be understood that the following examples are intended to describe various embodiments but are not intended to limit the embodiments in any way.

EXAMPLES

Example 1: Normalization of Excitation

In one example, the inclusion of fiducial marker(s) 116 (FIGS. 1 and 2) in digital images captured using a digital camera 104 (FIG. 1) allows the tissue image processing host computer 202 (FIG. 3) to compensate for variations in apparent optical excitation such as variations in excitation source to subject distance. The images $I_{1\ldots n}$ may have been acquired with different digital cameras 104, and/or with variations in and spatial and spectral sensitivity. Other variations might include distance to subject, focal length and optical axes. Ideally when digital images are captured, the excitation source 106 (e.g., flash) should be ON or illuminating the subject tissue 102, the optical normal of both the region of interest (e.g., lesion) and the fiducial marker 116 should be equal and perpendicular to the optical normal of the digital camera 104, however, this also must be accounted for. Variations might also be the result of ambient conditions and poor image quality. The reflection and the backscatter from the fiducial marker 116 enables the spectral distribution of the entire image to be registered by the tissue image processing host computer 202.

Example 2: Reflection vs. Backscatter

In one example, the tissue image processing host computer 202 (FIG. 3) characterizes the tissue response from various optical layers of tissue 102 (FIGS. 1 and 2) in order to be able to differentiate tissue variations that might not be fully visible to the naked eye. The spectra from two digital images are normalized using the fiducial marker 116 and/or areas of tissue 102 in some or all digital images where melanin or hemoglobin spectra appear normal. The spectral distribution is compared between either the whole digital image or a localized area of the digital image. With the major spectral components removed that contribute to reflection from the Epidermal Layer $I_1L_E$, the changes in other optical layers such as Melanin Layer $I_1L_M$, Hemoglobin Layer $I_1L_H$, Collagen Layer $I_1L_C$ or $I_1L_{CF}$ can be more easily compared.

Example 3: Spatial Distribution

In one example, low cost digital cameras 104 (FIG. 1) with minimal capacity for measuring spectral changes but adequate for accessing the shape and color or lesion borders are employed to capture digital images of the tissue 102. Correlation of digital images enables a clinician or automated system (e.g., tissue image processing host computer 202 of FIG. 3) to assess if there are morphological changes. These morphological changes would—subsequently be noted in the ABCD guidance of tissue evolution. The digital images timeline is corrected based on the fiducial marker(s) 116 appearing in the source image $I_1(x_n, y)$ and the fiducial marker(s) 116 appearing within the time series images $I_{1\ldots n}(x_n, y_n)$.

Example 4: Controlled Laboratory System and Analysis

In one example, a patient specific model generated by a tissue image processing host computer 202 (FIG. 3) allows cross reference between digital images in a timeline or sequence for the same patient. A useful analysis would determine if there is a relationship between spectral changes whether or not there has been any noticeable change in morphology. Once correction has been made for the optical tissue imaging system 100 (FIG. 1), and an image registration has been made, a time series of digital images can be compared. In an optical tissue imaging system 100 capable of being used with cut off filters, and with ambient conditions remaining similar, then regions of interest 118 (e.g., skin lesions) can be measured and a digital record of the digital image and/or measured information stored for later reference. In a time series of digital images, increases in NADH fluorescence, decreases of collagen fluorescence, physical scatter of light from tissue at various physical layers due to tissue density, spectral distribution due to size of cell nuclei, and changes in hemoglobin absorption due to increased blood flow or oxygenation may be combined in a diagnostic image layer. In some cases such digital images and associated information may be used to track tumor formation or be used as a screening tool.

Example 5: Single Image Compared to Phantom Image

In one example, rather than correcting a single digital image for morphologic changes, is the digital image is corrected for the digital image's spectral distribution compared to a tissue phantom. A tissue image processing host computer 202 (FIG. 3) breaks the digital image down into spectral layers. The resulting data is used as an input to the ABCD rules, where as part of the color analysis, the spectral distribution is compared to a standard and is reported as variations in the visible, Ultra Violet, Near Infra Red, with particular notes or emphasis on: any brown or black streaks; textures variations measured by reflection; and pink or red areas. The phantom image could be a baseline standard, could be an image taken on the subject in an area where there is no concern, or could be based on a projection of optical features of a fiducial marker 116 (FIGS. 1 and 2).

Example 6: Contrast Agent

In one example, a first digital image is captured before and a second digital image is captured after the use of a contrast agent such as a dye that combines with protein or bacteria, and/or after administration of a vasodilator, and/or a biomarker with a fluorescent marker, and/or acetic acid or water. The first and second digital images are combined and the difference is used to screen for the tissue or region of interest.

CONCLUSION

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other systems, not necessarily the exemplary tissue imaging and digital image processing system generally described above.

For instance, the systems, devices, and methods described herein may also be applied to other testing and/or analysis, including testing or analyzing the effect of various cosmetics or therapeutics on tissue, such as skin, to discern whether such cosmetics have a beneficial effect. For example, digital images may be captured of a region of interest (e.g., proximate the eyes, chin or mouth) both before application of a cosmetic or therapeutic material or treatment, and following such application or treatment. The tissue image processing host computer systems may analyze the digital images to assess the effect of the cosmetic or therapeutic material or treatment on the region of interest. For example, the tissue image processing host computer systems 202 may determine whether a level of hydration has been increased, whether a level of blood flow or oxygenation has increased, whether a total number of wrinkles have decreased, or size of wrinkles decreased, or whether blemishes have been reduced.

The system may be used to measure skin health or beauty, including surface and subsurface layers. For example, the system may be used to measure or otherwise assess a degree of hydration or a level or rate of blood flow, which could be further compared to collagen. Alternatively, or additionally, the system may measure or otherwise assess a total number of wrinkles in a given area and/or size of such wrinkles, and/or a total number of blemishes in a given area and/or size of such blemishes.

In particular, the wavelength ratios of the optical layers could be used to characterize a skin hydration assessment between two images at different times. This could be used with a fixed optical set up that includes optical excitation sources located at different fixed angles to better access skin reflection. Such can be measured with either a physical or projected fiducial marker scatter layer employed. For instance a projected marker, if it were linear and monochromatic, would have variable scatter along its axes. The excitation wavelength of this fiducial marker could be varied to include reference to other optical layers such as the water absorption layer, the hemoglobin absorption layer, and the collagen absorption layer. If such a linear and monochromatic fiducial marker were compared over a series or sequence of digital images, the ability to characterize the skin surface, such as wrinkles, and the skin health such as hydration, blood flow and collagen, could be visually presented, for example as indices, graphs or as comparative images.

Such a system could be used as a standardized approach to determine the health and beauty impacts of various cosmetics, moisturizers, therapeutic materials, other skin creams, and/or therapeutic treatments. Such may be advantageously employed in clinical trials or for use in point of sale retail facilities where an individual's skin could be assessed and the indices of skin health or beauty could be used for product selection. Results of such an assessment may be presented in a visual form, for example a display or printout of indices, graphs or comparative images.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. The present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms taught herein are capable of being distributed as a program product in a variety of forms, and that an illustrative embodiment applies equally regardless of the particular type of nontransitory signal bearing storage media used to actually carry out the distribution. Examples of nontransitory signal bearing storage media include, but are not limited to, the following: recordable type media such as floppy disks, hard disk drives, CD ROMs, digital tape, and computer memory; and other non-transitory computer-readable storage media.

The various embodiments described above can be combined to provide further embodiments. All of the U.S. patents, U.S. patent application publications, U.S. patent applications, foreign patents, foreign patent applications and non-patent publications referred to in this specification and/ or listed in the Application Data Sheet, including U.S. provisional patent application Ser. No. 61/311,750, filed Mar. 8, 2010, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

I claim:

1. A fiducial marker for use in tissue imaging, comprising: a substrate having a defined profile and bearing a plurality of sections having respective wavelength selective absorption, reflectance or florescence characteristics, at least a first number of the sections form a color chart of a plurality of different colors and at least a second number of the sections are optical phantoms that match respective ones of a number of spectral characteristics of living tissue, wherein a first set of the sections includes a first color chart having a black section, a white section, a plurality of sections each of which is a respective shade of grey and a plurality of sections each of which is a respective one of a plurality of additional colors, all the sections of the first set overlaid by a scattering layer, and a second set of the sections includes a second color chart having a black section, a white section, a plurality of sections each of which is a respective shade of grey and a plurality of sections each of which is a respective one of a plurality of additional colors, none of the sections of the second set overlaid by a scattering layer.

2. The fiducial marker of claim 1 wherein the scattering layer overlaying all of the sections of the first set of sections has a number of characteristics that simulate a number of optical characteristics of at least one layer of the living tissue.

3. The fiducial marker of claim 2 wherein the optical characteristics are those of skin.

4. The fiducial marker of claim 2 wherein the second number of the sections includes at least one of a first section having a selective spectral absorption at a waveband of about 330 nm to about 500 nm, a second section having a selective spectral absorption at a wavelength at about 415 nm, about 515 nm, or about 590 nm, a third section having a selective spectral absorption at a waveband of about 340 nm to about 400 nm, a fourth section having a selective spectral fluorescence at a waveband of about 450 nm to about 550 nm, or a fifth section having a selective spectral absorption at about 550 nm, about 630 nm, about 730 nm, or about 820 nm or a reflection peak at about 514 nm, about 606 nm or about 739 nm.

5. The fiducial marker of claim 4 wherein the fourth section includes at least one of fluorescein or 5-carboxyfluorescein.

6. The fiducial marker of claim 2 wherein the second number of the sections includes each of a melanin layer phantom section having a selective spectral absorption at a waveband of about 330 nm to about 500 nm, a hemoglobin layer phantom section having a selective spectral absorption at a wavelength at about 415 nm, about 515 nm, or about 590 nm, a first collagen layer phantom section having a selective spectral absorption at a waveband of about 340 nm to about 400 nm, a second collagen layer phantom section having a spectral fluorescence at a waveband of about 450 nm to about 550 nm, and a fifth section having a selective spectral absorption at about 550 nm, about 630 nm, about 730 nm, or about 820 nm or a reflection peak at about 514 nm, about 606 nm or about 739 nm.

7. The fiducial marker of claim 1 wherein the defined profile is a polygon.

8. A system to image bodily tissues, the system comprising:

a physical fiducial marker selectively positionable at least proximate a region of interest on a portion of a bodily tissue to be imaged, the physical fiducial marker including a substrate having a defined profile and bearing a plurality of sections having respective wavelength selective absorption, reflectance or florescence characteristics, at least a first number of the sections form a color chart of a plurality of different colors and at least a second number of the sections are optical phantoms that match respective ones of a number of spectral characteristics of living tissue; wherein a first set of the sections includes a first color chart having a black section, a white section, a plurality of sections each of which is a respective shade of grey and a plurality of sections each of which is a respective one of a plurality of additional colors, all the sections of the first set overlaid by a scattering layer, and a second set of the sections includes a second color chart having a black section, a white section, a plurality of sections each of which is a respective shade of grey and a plurality of sections each of which is a respective one of a plurality of additional colors, none of the sections of the second set overlaid by a scattering layer, at least one light source operable to project a virtual fiducial marker at least proximate the region of interest on the portion of the bodily tissue to be imaged, the virtual fiducial marker having a defined profile and a plurality of defined shapes; and an image capture device having a field of view and configured to capture digital images of bodily tissue including the region of interest, the physical fiducial marker and the virtual fiducial marker all encompassed by the field of view of the image capture device.

9. The imaging system of claim 8 wherein the virtual fiducial marker is projected with the plurality of defined shapes as straight line segments.

10. The imaging system of claim 8 wherein the virtual fiducial marker is projected with the profile of a circle and with the plurality of defined shapes as straight line segments emanating from a center point of the circular profile.

11. The imaging system of claim 10 wherein the defined profile of the physical fiducial marker is a polygon.

* * * * *